US012036024B2

United States Patent
Popov et al.

(10) Patent No.: US 12,036,024 B2
(45) Date of Patent: Jul. 16, 2024

(54) SYSTEM AND METHOD FOR QUANTIFICATION OF EXERCISE AND PHYSICAL THERAPY

(71) Applicant: President and Fellows of Harvard College, Cambridge, MA (US)

(72) Inventors: Dmitry Popov, Somerville, MA (US); Michael Karpelson, Newton, MA (US); Timothy Walsh, Andover, MA (US); Conor Walsh, Cambridge, MA (US); Ryan Gulland, Somerville, MA (US); Alex Beaudette, Jamaica Plain, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 369 days.

(21) Appl. No.: 17/432,528

(22) PCT Filed: Feb. 27, 2020

(86) PCT No.: PCT/US2020/020172
§ 371 (c)(1),
(2) Date: Aug. 20, 2021

(87) PCT Pub. No.: WO2020/176773
PCT Pub. Date: Sep. 3, 2020

(65) Prior Publication Data
US 2022/0133198 A1 May 5, 2022

Related U.S. Application Data

(60) Provisional application No. 62/811,314, filed on Feb. 27, 2019.

(51) Int. Cl.
*A63B 21/00* (2006.01)
*A61B 5/22* (2006.01)
(Continued)

(52) U.S. Cl.
CPC ........ *A61B 5/224* (2013.01); *A63B 21/00043* (2013.01); *A63B 21/00185* (2013.01);
(Continued)

(58) Field of Classification Search
CPC ... A61B 5/224; A61B 2505/09; A61B 5/1107; A63B 21/00043; A63B 21/00185;
(Continued)

(56) References Cited

U.S. PATENT DOCUMENTS 6,491,647 B1 12/2002 Bridger et al.
7,072,789 B2 7/2006 Vock et al.
(Continued)

OTHER PUBLICATIONS

P. Grabowski, et al., "The kiio Sensor; A New Innovation For Assessment of Muscle Function," PT Aligned <online at http://news.meyerpt.com/physical-therapists/misc/kiio-sensor-new-innovation-assessment-muscle-function/, visited Sep. 7, 2021> (Nov. 2, 2017).
(Continued)

*Primary Examiner* — David J Bolduc
(74) *Attorney, Agent, or Firm* — Modern Times Legal; Robert J. Sayre

(57) ABSTRACT

A system for quantification of exercise and physical therapy includes an anchoring module and an electronics module. The anchoring module is removably attached to an object (e.g., a flexible resistive band) or equipped with a clamping mechanism for removably securing the object. The anchoring module also includes an anchoring-module coupling fixture. At least one of the modules includes a sensor (e.g., a force sensor) configured to generate a signal representative of a user's performance during exercise or physical therapy; a processor configured to receive signals from the force sensor; a computer storage medium storing software code and in communication with the processor, wherein the software code includes instruction for processing the signals from the force sensor to quantify the performance; and at
(Continued)

least one electronics-module coupling fixture configured to secure the electronics module to the anchoring module coupling fixture.

41 Claims, 16 Drawing Sheets

(51) Int. Cl.
  *A63B 21/04*    (2006.01)
  *A63B 21/055*   (2006.01)
  *A63B 71/06*    (2006.01)

(52) U.S. Cl.
  CPC ...... *A63B 21/0442* (2013.01); *A63B 21/0552* (2013.01); *A63B 21/4034* (2015.10); *A63B 21/4035* (2015.10); *A61B 2505/09* (2013.01); *A63B 2071/0625* (2013.01); *A63B 2071/0647* (2013.01); *A63B 2071/0655* (2013.01); *A63B 2209/08* (2013.01); *A63B 2220/72* (2013.01); *A63B 2220/801* (2013.01); *A63B 2220/802* (2013.01); *A63B 2220/803* (2013.01); *A63B 2220/805* (2013.01); *A63B 2225/74* (2020.08); *A63B 2230/06* (2013.01); *A63B 2230/75* (2013.01)

(58) Field of Classification Search
  CPC ............ A63B 21/0442; A63B 21/0552; A63B 21/4034; A63B 21/4035; A63B 2071/0625; A63B 2071/0647; A63B 2071/0655; A63B 2209/08; A63B 2220/72; A63B 2220/801; A63B 2220/802; A63B 2220/803; A63B 2220/805; A63B 2225/74; A63B 2230/06; A63B 2230/75; A63B 21/072; A63B 71/0054; A63B 71/0622; A63B 2071/065; A63B 2209/10; A63B 2220/12; A63B 2220/20; A63B 2220/30; A63B 2220/40; A63B 2220/51; A63B 2220/808; A63B 2220/833; A63B 2220/836; A63B 2225/20; A63B 2225/50
  See application file for complete search history.

(56) References Cited

U.S. PATENT DOCUMENTS

| | | |
|---|---|---|
| 7,162,392 B2 | 1/2007 | Vock et al. |
| 9,409,053 B1 | 8/2016 | Todd |
| 2003/0060340 A1 | 3/2003 | Freeman |
| 2008/0119763 A1 | 5/2008 | Wiener |
| 2009/0062092 A1 | 3/2009 | Mortimer |
| 2010/0004061 A1 | 1/2010 | Merril et al. |
| 2011/0082394 A1* | 4/2011 | Chiu .................. A61B 5/7264 600/595 |
| 2011/0251021 A1* | 10/2011 | Zavadsky .............. A63F 13/28 482/5 |
| 2012/0202659 A1 | 9/2012 | Wroclawsky |
| 2012/0302406 A1 | 11/2012 | Hinds et al. |
| 2013/0065680 A1* | 3/2013 | Zavadsky ............. A63F 13/211 463/30 |
| 2014/0323271 A1* | 10/2014 | Hinds ................ A63B 21/4043 482/8 |
| 2014/0336947 A1 | 11/2014 | Walke et al. |
| 2017/0304679 A1* | 10/2017 | Orfield .............. A63B 21/0724 |
| 2018/0310659 A1* | 11/2018 | Poupyrev ............ A63B 43/004 |
| 2021/0213329 A1* | 7/2021 | Wechsler ........... A63B 21/4035 |
| 2021/0236870 A1* | 8/2021 | Bergengren ....... A63B 21/0056 |
| 2021/0370122 A1* | 12/2021 | Mohieldin ......... A63B 21/0552 |
| 2022/0233905 A1* | 7/2022 | Bar .................... A63B 21/1618 |

OTHER PUBLICATIONS

PC Tech, "Meet ResisTrack: The world's 1st muscle fitness tracker & motivator," PC Tech Magazine <online at https://pctechmag.com/2015/05/meet-resistrack-the-worlds-1st-muscle-fitness-tracker-motivator/, visited Sep. 7, 2021> (May 21, 2015).
D. Belic, "Resistrack is a smartphone-connected muscle training device," MHealthSpot <online at https://mhealthspot.com/2015/05/resistrack-smartphoneconnected-muscle-training-device/, visited Sep. 7, 2021> (May 25, 2015).
D. Thompson, "Circuband iQ: Our Resistance Band with NASA Grade Sensors," Kickstarter <online at https://www.kickstarter.com/projects/814410015/circuband-iq-all-in-one-home-gym-with-muscle-track, visited Sep. 7, 2021> Oct. 4, 2017).
LiftUp, "LiftUp: Strength training reimagined," <online at https://www.kickstarter.com/projects/getliftup/liftup-a-modern-resistance-band-that-tracks-your-w/, visited Sep. 7, 2021> (Apr. 21, 2016).
B. Dobkin, "A Rehabilitation-Internet-of-Things in the Home to Augment Motor Skills and Exercise Training," 31 Neurorehabilitation and Neural Repair, 217-227 (Nov. 24, 2016).
P Nicolson, et al., "Self-reported Home Exercise Adherence: A Validity and Reliability Study Using Concealed Accelerometers," 48 J. of Orthopaedic & Sports Physical Therapy, 943-950 & appendices (Dec. 2018).

* cited by examiner

SYSTEM AND METHOD FOR QUANTIFICATION OF EXERCISE AND PHYSICAL THERAPY

BACKGROUND

The discussion of the background state of the art, discussed below, may reflect hindsight gained from the disclosed invention(s); and these characterizations are not necessarily admitted to be prior art.

A resistance band is an elastic band used for strength training. Resistance bands are now used widely as part of exercises conducted for muscle rehabilitation, general fitness and strength training. Typically, the bands are color coded to show different levels of resistance and users need to select an appropriate level. Code colors can vary between brands so users must pick an appropriate level if purchasing their own bands rather than relying just on color. Also available are loop bands as well as tubing without handles and bands set up with handles (a common option for many purchasers).

The National Sporting Goods Association reports that, if taking into account only the sporting goods market, 3,850,000 units of resistance bands were sold in 2017, which represents a 7% increase in sales from 2015 to 2016, which represented the biggest growth among home exercise equipment, with dumbbells showing 0% increase and weight machines showing a 2% increase.

Beyond being a popular item for fitness, the use of resistance bands can be highly advantageous in physical therapy for rehabilitation of joints and muscles. However, when an individual is assigned the use of resistance bands at home to rehabilitate an injury, fitness-band use typically is not fully optimized. There is no known method available on the market to track the progress a patient makes with resistance bands, including the force applied when stretching the band.

SUMMARY

A system and method for quantification of exercise and physical therapy are described herein, where various embodiments of the system and method may include some or all of the elements, features and steps described below.

A system for quantification of exercise and physical therapy includes an anchoring module and an electronics module. The anchoring module is removably attached to an object (e.g., a flexible resistive band) or equipped with a clamping mechanism for removably securing the object. The anchoring module also includes an anchoring-module coupling fixture. At least one of the modules includes a sensor (e.g., a force sensor) configured to generate a signal representative of a user's performance during exercise or physical therapy (e.g., including force applied by the user); a processor configured to receive signals from the sensor; a computer storage medium storing software code and in communication with the processor, wherein the software code includes instruction for processing the signals from the sensor to quantify the user's performance; and at least one electronics-module coupling fixture configured to secure the electronics module to the anchoring module coupling fixture.

Another exemplification of the system includes an anchoring module, including a clamping mechanism that includes at least one spring-loaded cam cleat configured for removably securing the anchoring module to an object; and an electronics module. At least one of the modules includes a sensor (e.g., a force sensor) configured to generate a signal representative of the user's performance during exercise or physical therapy; a processor configured to receive signals from the said sensor; and a computer storage medium storing software code and in communication with the processor, wherein the software code includes instruction for processing the signals from the sensor to quantify the user's performance, wherein the anchoring module extends from or is configured for attachment to the electronics module.

A method for quantification of exercise and physical therapy using the above system includes (a) securing an object using the clamping mechanism of the anchoring module, (b) applying a force to the object via performance of the exercise or physical therapy, (c) using the sensor to quantify the performance of exercise or physical therapy, and (d) displaying a representation of the quantified performance.

The system and methods described herein can quantify an exercise with free body motion, with a flexible resistive element, and/or using a constant weight, such as a dumbbell, extracting such data as number of repetitions, range of motion, time spent in a given position, deviation from a given position, applied force, produced power, percentage of stretch, amount of stretch, smoothness of motion, range of motion, speed, etc. The system and method can also be used to detect the form of motion while exercising with free body motion, with a flexible resistive element, and/or using a constant weight, such as a dumbbell.

The system and methods can provide anchoring to a flexible resistive element and/or to a wearer's body and/or to a constant weight, such as a dumbbell. The system can be in modular form, facilitating its adaptation for use with any exercise with free body motion and/or using a flexible resistive element, as well as using a constant weight, such as a dumbbell. The system and method can quantify the force applied to a flexible resistive element and/or the deformation of the flexible resistive element.

Using this technology within clinics and hospitals, a physical therapist can provide a more dynamic and efficient therapy as well as improve adherence to the therapy. Another application for this technology is to employ it outside of a clinic or hospital environment, such as in a patients' homes. In particular, the system and methods can offer a great benefit among the elderly population for performing training. We are presented with a crisis of sorts as more and more of the population in the United States and in other countries lives longer. In addition to individual life expectancy increasing, a large percentage of the population is older and aging. The healthcare system is expected to be stressed to its capacity in providing services to the elderly, and society may not have enough physicians to meet the demand of this elderly population. One way to lift this burden is to develop methods that allow physicians to see more individuals. Connected health/telehealth/remote-monitoring sensors and systems, such as is described herein, can alleviate this stress by providing additional tools to monitor a larger number of patients per therapist. Further still, data from the system can be monitored by health-insurance companies to monitor for plateaus in the results from medical treatment and physical therapy. In additional exemplifications, the systems and methods can be used to serve the global home-fitness market, including use with fitness apps, aerobic trackers, smart clothing, and connected training machines.

Figure 1:
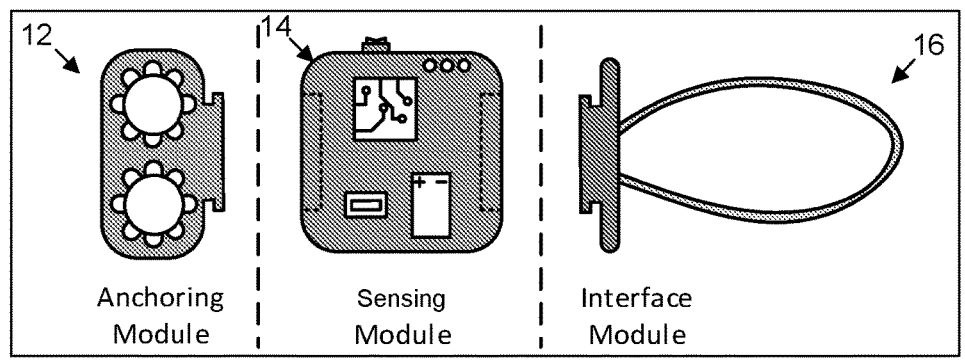
FIG. 1 shows an exemplification of an anchoring module 12, an electronics module 14, and an interface module 16 of a system for quantifying exercise and physical therapy.

In the accompanying drawings, like reference characters refer to the same or similar parts throughout the different views; and apostrophes are used to differentiate multiple instances of the same item or different embodiments of items sharing the same reference numeral. The drawings are not necessarily to scale; instead, an emphasis is placed upon illustrating particular principles in the exemplifications discussed below. For any drawings that include text (words, reference characters, and/or numbers), alternative versions of the drawings without the text are to be understood as being part of this disclosure; and formal replacement drawings without such text may be substituted therefor.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially (though not perfectly) pure, as practical and imperfect realities may apply; e.g., the potential presence of at least trace impurities (e.g., at less than 1 or 2%) can be understood as being within the scope of the description. Likewise, if a particular shape is referenced, the shape is intended to include imperfect variations from ideal shapes, e.g., due to manufacturing tolerances. Percentages or concentrations expressed herein can be in terms of weight or volume. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. The term, "about," can mean within ±10% of the value recited. In addition, where a range of values is provided, each subrange and each individual value between the upper and lower ends of the range is contemplated and therefore disclosed.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limited to exemplary embodiments. As used herein, singular forms, such as those introduced with the articles, "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

Figure 22:
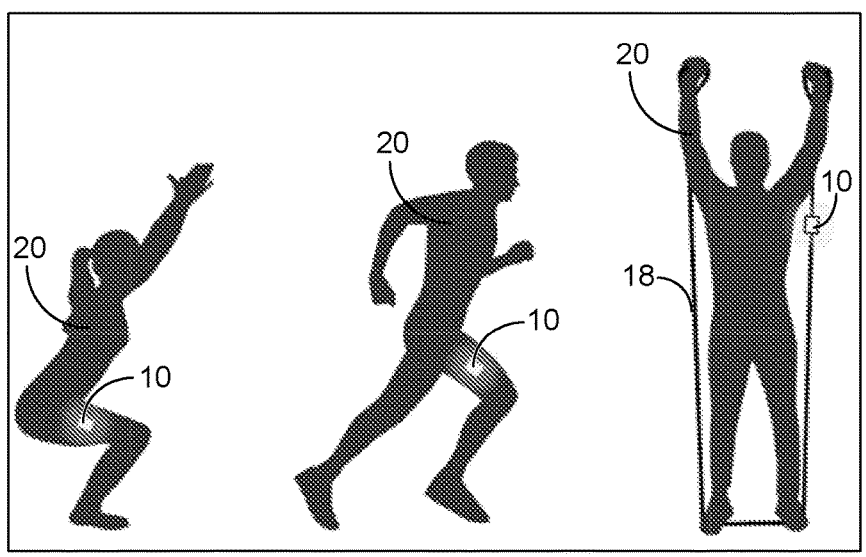
FIG. 22 shows a user 20 wearing a system 10 with at least one sensor and using a resistive band 18 incorporating a system 10 with at least one sensor.

The system described herein can use one or more systems 10 with sensors that anchor onto a wearer's body and/or onto a resistive flexible element 18 and quantify motions performed during free-body exercise and/or with the resistive flexible element 18, as shown in FIG. 22. Methods of anchoring the system 10 onto the body of a user 20 and/or onto a resistive flexible element 18 can vary. Combinations and configurations of the sensors utilized in the overall system 10 can vary. To provide an understanding of how the system 10 can work and appear, various embodiments and their configuration and functions are described, below.

The system 10 can include the following interlocking (or integrally joined) modules (shown in FIG. 1), where each module has its own core function:
- an anchoring module 12 that provides a secure anchoring to a flexible resistive element, to a constant weight, to a wearer's body, or to the surroundings;
- an electronics module 14 that contains electronics, ports, and a battery; and
- an interface module 16 that provides means for a user to interact with the system and can be in the form of, e.g., a flexible strap or rigid.

Any of the above-described modules may include input/output electronics components for the user interface, such as lights or switchers, as well as sensors (e.g., a sensor that measures any of the following: force, displacement, touch, temperature, sound, etc.) that have to be connected to the electronics module to be powered and to collect data.

Figure 2:
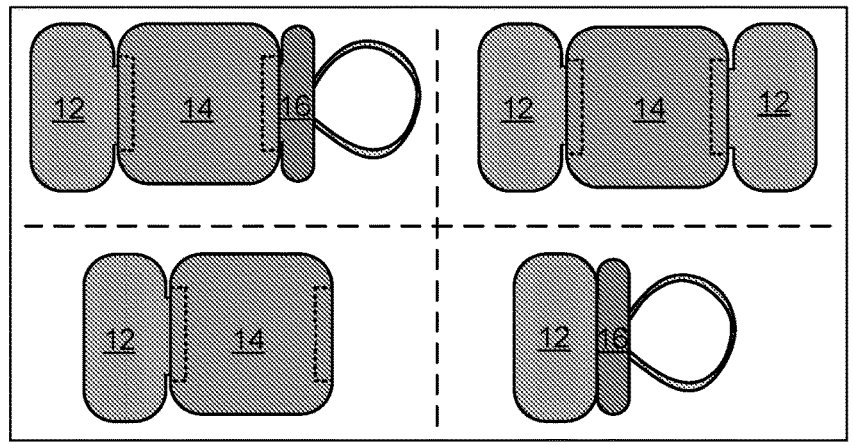
FIG. 2 shows how the modules 12, 14, and 16 of FIG. 1 can interface in various alternative configurations.

These modules 12, 14, and 16 can interface with each other in various configurations, as shown in FIG. 2. The system can include multiple modules of the same type. The modules 12, 14, and 16 can interlock with one another in a variety of ways, e.g.:
- by sliding via open sliding rails;
- by using buttons or clips;
- by using magnets;
- by being placed in a cavity of one of the modules;
- by clasping onto one of the modules; and/or
- by using high-friction materials, such as VELCRO hook-and-loop fasteners.

Figure 23:
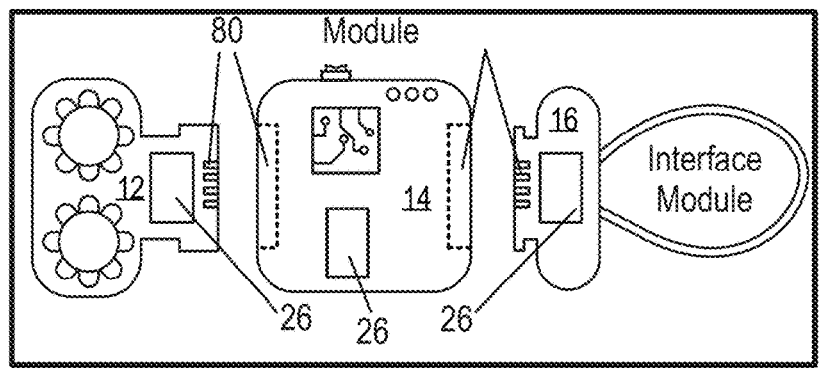
FIG. 23 shows alternative exemplifications in which a force sensor 26 is respectively located in an anchoring module 12, in an electronics module 14, and in an interface module 16.

Modularity of the system 10 is an advantageous feature that enables the system to be versatile. The system can include a variety of sensors including a force sensor that directly measures applied force (additional description of the types of sensors the system may include is presented, infra). A sensor 26, such as a force sensor, can be located in either the anchoring, electronics or interface module 12, 14, or 16, as shown in FIG. 23. If located in the anchoring or electronics module 12 or 14, the sensor 26 incorporates electrical connections 80 to selectively engage with electrical connections 80 of the electronics module 14 so that data can be collected via the electronics module 14. Since, in many cases, the anchoring module 12 is designed to be used with one type of equipment (e.g., a resistance band, dumbbell, medicine ball, etc.), and the interface module 16 is designed for one type of interaction with a wearer's body (e.g., via a chest strap or wrist band), configurations with sensors located in the anchoring or interface modules 12 or 16 enable multipurpose usage of the electronics module 14. A single electronics module 14 can interlock with any of a variety of anchoring or interface modules 12 or 16, wherein each anchoring or interface module 12 or 16 has its own sensor and purpose. This approach keeps the low form factor of the electronics module 14 and makes it feasible to place the electronics module 14 on a wearer's body by means of an interface module 16 to track free-body motions. Keeping all of the sensors in the electronics module 14 would result in a big and obstructive design that would unlikely be easily worn or attached to different parts of the body. Additionally, this approach extends the lifetime of the system, where each module and/or sensor can be replaced with an improved version without a need to update the entire system. Also, a new gear and/or sensor can expand the range of applications and features by seamlessly integrating into such a modular system.

Figure 10:
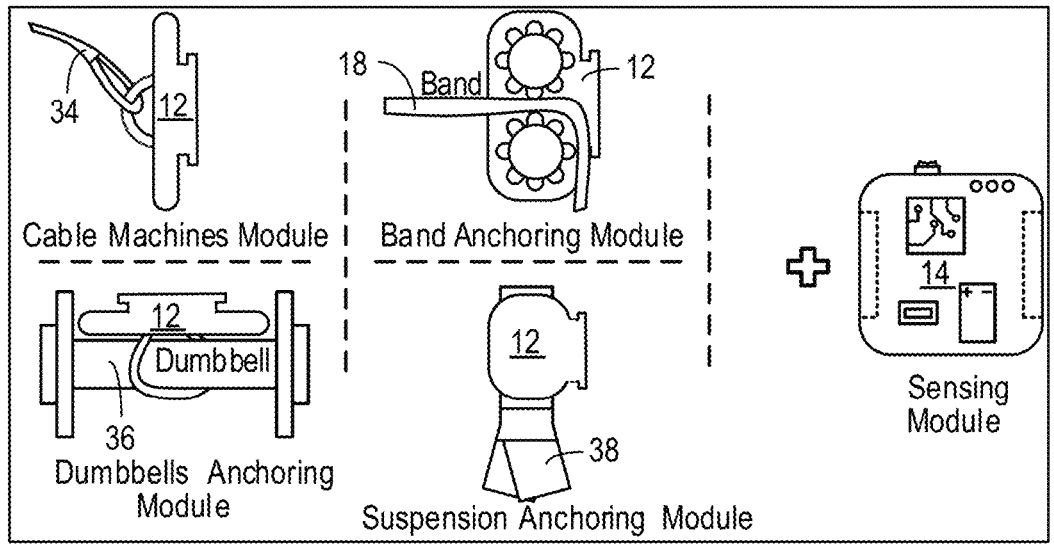
FIG. 10 shows various different configurations of the anchoring and electronics modules 12 and 14 for different exercise scenarios.

As shown in FIG. 10, a user can attach different designs of interlocking or integrally joined anchoring modules to:
- a flexible resistive element 18 (via mechanisms described, below);
- a constant weight 36, such as a dumbbell (by means of a loop-like connector); or
- a cable 34 of a cable machine (by means of a flexible or a rigid connector);

or in additional exemplifications to:
- a suspension band 38 of a suspension training system (by means of a flexible or a rigid connector similar to the one used with the flexible resistive element 18 and as described further); or
- any object that can be moved during an exercise or physical therapy.

Figure 24:
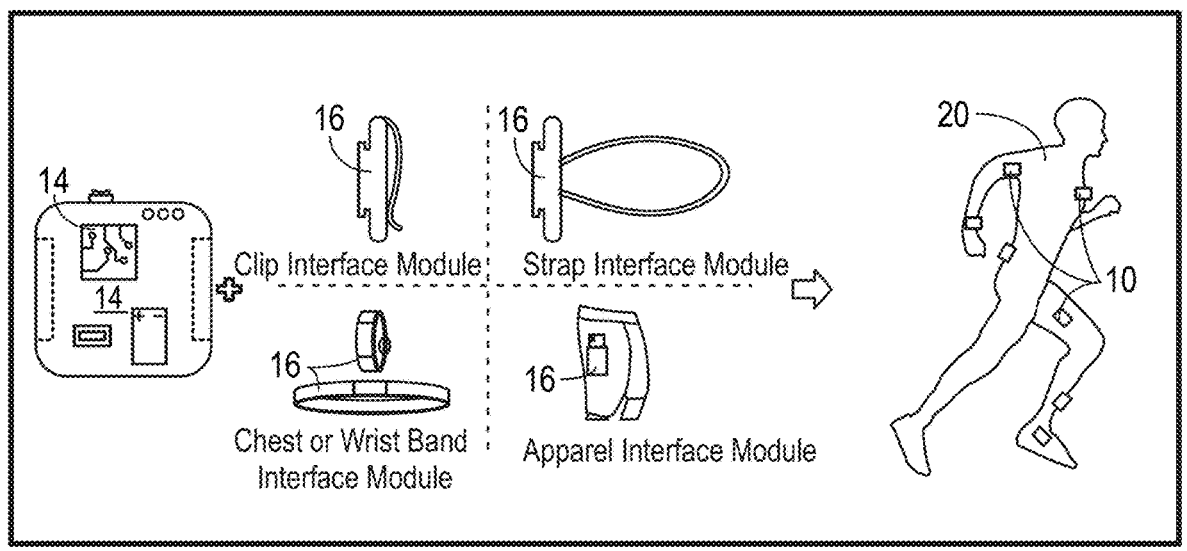
FIG. 24 shows different options for attaching an interlocking or integrally joined interface module 16 to a wearer's body, including to a chest or wrist/arm band or to apparel (e.g., to exercise shorts worn by the user) to position the electronics module at any of the exemplary positions shown at right.

As shown in FIG. 24, a user 10 can attach different designs of interlocking or integrally joined interface modules 16 to a wearer's body at different locations that may include, but are not limited to, a wrist, chest, leg, waist, foot, arm, head, etc. Interface modules 16 can be in the form of a single-piece rigid or elastic component or can comprise multiple parts.

This modular approach enables a single platform that allows a user 20 to quantify a variety of exercise scenarios including but not limited to: push-ups, biceps curls, tricep extensions, lateral raises, shoulder extensions, rear flys, contra-stabilized latissimus-dorsi pulldowns, chest presses, contra-stabilized rows, contra-stabilized rear flys, overhead presses, low rows, high rows, shoulder flexions, plantarflexions, single-leg plantarflexions, squats, single-leg squats, split lunges, rear lunges, forward lunges, side lunges, monster walks, hip abductions, hamstring curls, hip extensions, hip flexions, knee extensions, deadlifts, single-leg deadlifts, hip bridges, single-leg bridges, Superman extensions, quadruped contralaterals, quadruped unilaterals, swimming, Russian twists, dead-bug contralaterals, dead-bug unilaterals, side planks on knees, side planks with one leg straight, side planks with straight leg and staggered feet, and side planks with straight legs stacked.

Figure 3:
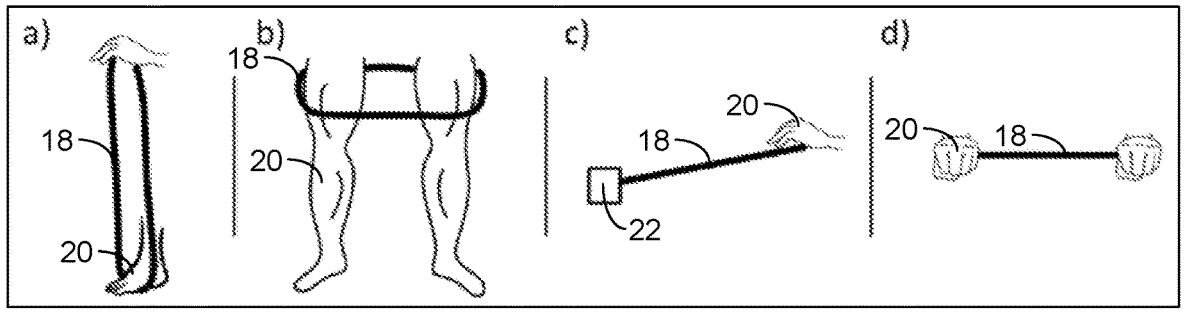
FIG. 3 shows a user 20 engaging in a variety of exercise scenarios using a resistive element 18.

Flexible resistive elements 18 are used for training and rehabilitation in various scenarios and, therefore, the modularity of the present system 10 is an advantageous feature for use therewith. FIG. 3 depicts four basic scenarios of using a flexible resistive element 18, where, in cases (a) and (b), the resistive element 18 forms a "loop" that can encircle, e.g., the user's hand, feet, leg(s), etc., and in cases (c) and (d); the resistive element 18 creates a straight line between two fixed points (e.g., between the user's hand and a fixed object or between the user's hands).

Figure 4:
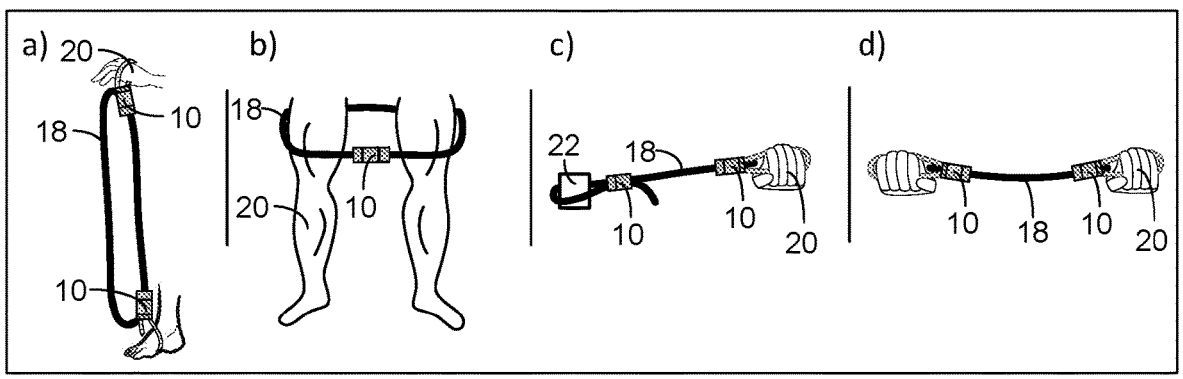
FIG. 4 shows a variety of exercise scenarios, similar to those shown in FIG. 3 using the system 10 described herein in combination with a resistive element 18.

FIG. 4 shows how the proposed system 10 can be applied to the exercise scenarios described above. There is no functional difference between cases (a) and (d), where two sets 10 of modules anchor to a resistive element 18 and a user 20 applies forces by using either of two limbs. In case (c), one of the sets 10 of modules is used as a static anchor point. It enables the same features as in cases (a) and (d) and also secures and releases a resistive element 18 to and from a surrounding environment. Since there is no need to make a node, this configuration saves preparation time and prolongs the lifetime of the resistive element. In case (b), one anchoring module 12 attached to an electronics module 14 or two anchoring modules 12 are interlocked with an electronics module 14 mounted therebetween, allowing for the overall system 10 to be placed in the middle of the resistance element 18. The system 10 in this case can still enable the same features and gather the same data as in all other cases.

For ease of explanation henceforth, one set of modules that provides a single anchor point and, therefore, reaction forces will be referred to as a "clamp".

Figure 32:
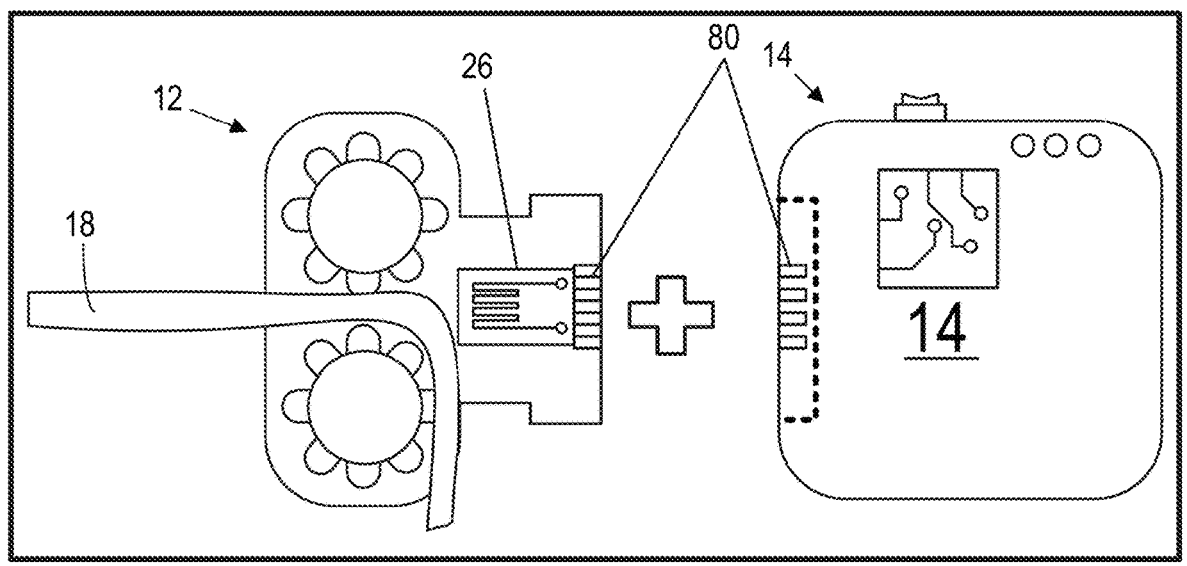
FIG. 32 shows a quick-setup exemplification of the system, wherein a force sensor 26 is located within the band-anchoring module 12 and has electrical connections 80 to selectively engage with the electrical connections of the electronics module 14 when the two modules 12 and 14 are interlocked.

A first exemplification, employing a clamp, represents an approach that focuses on quick setup and user-friendliness of a unitary one-piece anchoring module 12. In this exemplification, a force sensor 26 is located within the band-anchoring module 12 and has electrical connections 80 to selectively engage with the electrical connections 80 of the electronics module 14 when two modules are interlocked, as shown in FIG. 32.

Figure 33:
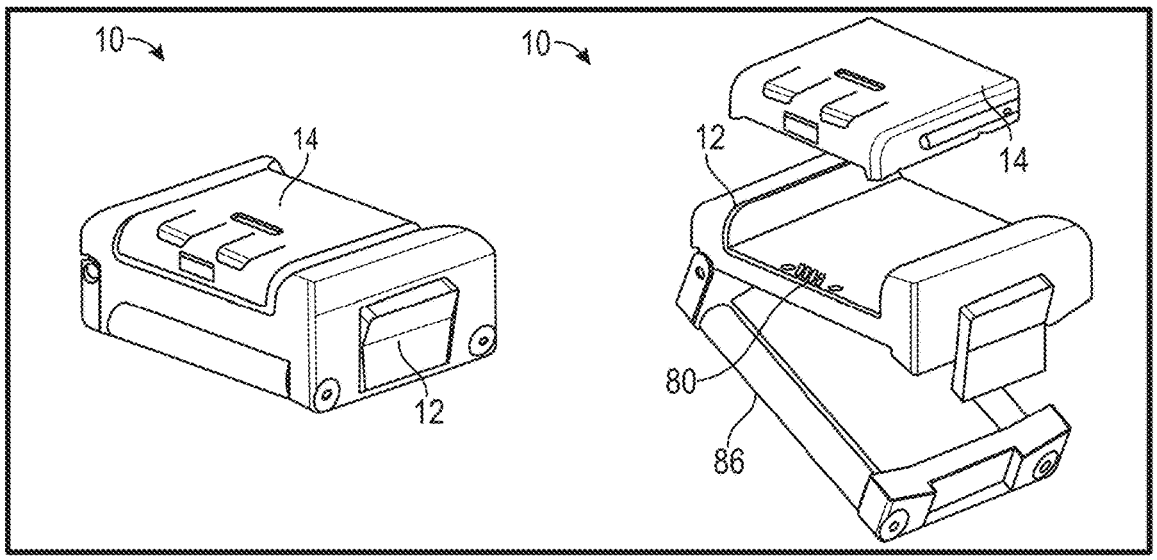
FIG. 33 is an image of another quick-setup exemplification of the system.

Another image of the quick-setup exemplification of the system 10 is shown in FIG. 33. The combination of anchoring and electronics modules 12 and 14 enables measurement of the forces applied onto a resistance band 18 (or another flexible resistive element). The anchoring module 12 utilizes a simple clasping mechanism, and it can clip onto resistive elements 18 of various widths. The anchoring module 12 incorporates a strain gauge 26 and two rollers 86 at the edges of the module 12 to measure the forces applied to a resistive element 18. The anchoring module 12 interfaces with an interlocking electronics module 14 via electrical connections to power the strain gauge 26 and to read a signal and collect, store, process, and/or communicate data. Electrical connections 80 can be implemented in the form of, but are not limited to, electrical pins, sliding contacts, magnetic contacts, spring loaded pins, keyed connectors, locked connectors, etc. The electronics module 14 can interlock with the anchoring module 12 in any of a variety of ways, including:
- by sliding into the anchoring module via open sliding rails on the top;
- by using buttons or clips;
- by using magnets;
- by being placed in a caveat of the anchoring module;
- by clasping onto the anchoring module; and
- by using high-friction materials, such as VELCRO hook-and-loop fasteners.

As mentioned earlier, such a configuration can be used to configure an electronics module 14 as a stand-alone sensor to track free-body motion exercises when attached directly to a user 20. Such modularity and connectivity features are advantageous for enabling the tracking of functional and free-body motion exercises, as combining two features of the two modules into a single system may result in a big and obstructive design that would unlikely to be easily worn or attached to different parts of the body.

This configuration can confer the following advantages:
- providing a simplified and streamlined user experience—e.g., the user may hold the device in one hand, insert the resistance band with the other hand, and immediately secure the clamp by squeezing the device together;
- enabling the device to be used with loop-style resistance bands without cutting the band; and
- enabling the device to be compact.

Full assembly of the exemplification includes the following components (FIG. 34):
- top frame 88: a primary structural member of the anchoring module 12 that mounts a clasp 96, hinge 84, mini printed circuit board (PCB) 90, and strain-gauge shield 110;
- a bottom frame 98: a structural support and exterior enclosure of the anchoring module 12;
- a strain gauge 26: an off-the-shelf component that measures force that is typically used in bodyweight scales;

a mini PCB 90: interfaces with the strain gauge 26 to spring contacts to connect with the electronics module 14;

a strain-gauge shield 110: locates the strain gauge 26 and retains the mini PCB 90 onto the top frame 88;

a center bar 92: transmits forces from the resistive element 18 to the strain gauge 26;

a clasp pin 95: acts as a hinge for the clamp 30;

a torsional spring 94: engages the clamp 30 to prevent it from accidentally opening;

a clasp 96: holds the top and bottom frames 88 and 98 together around the resistive element 18 and opens by pressing on a protruding upper portion;

a hinge pin 82: a pin that, when pressed, creates a hinge and allows opening of the anchor module 12 and replacing the resistive element 18;

rollers 86: roll on shoulder bolts 100, creating a low-friction surface so that tension in the resistive element 18 is transmitted directly to the center bar 92 and consequently to the strain gauge 26;

shoulder bolts 100: create a sturdy axle for the rollers 86 and provide structural support to the bottom frame 98;

a main printed circuit board 91: mechanically supports and electrically connects all of the electronic components, such as an IMU, a processor, amplifiers, etc., and provides electronic functionality to the device;

a haptic motor 104: provides haptic feedback to users 20;

a light pipe 106: provides diffused light from LEDs on the interior side of the electronics enclosure 108;

an electronics enclosure 108: a mounting place for the main printed circuit board 91, light pipe 106, and haptic motor 104; it utilizes cantilevered flexures to create tactile buttons; and electronics cover 102: retains the main printed circuit board 91 and battery 46 in an electronics enclosure 108 and provides an exterior surface.

Figure 34:
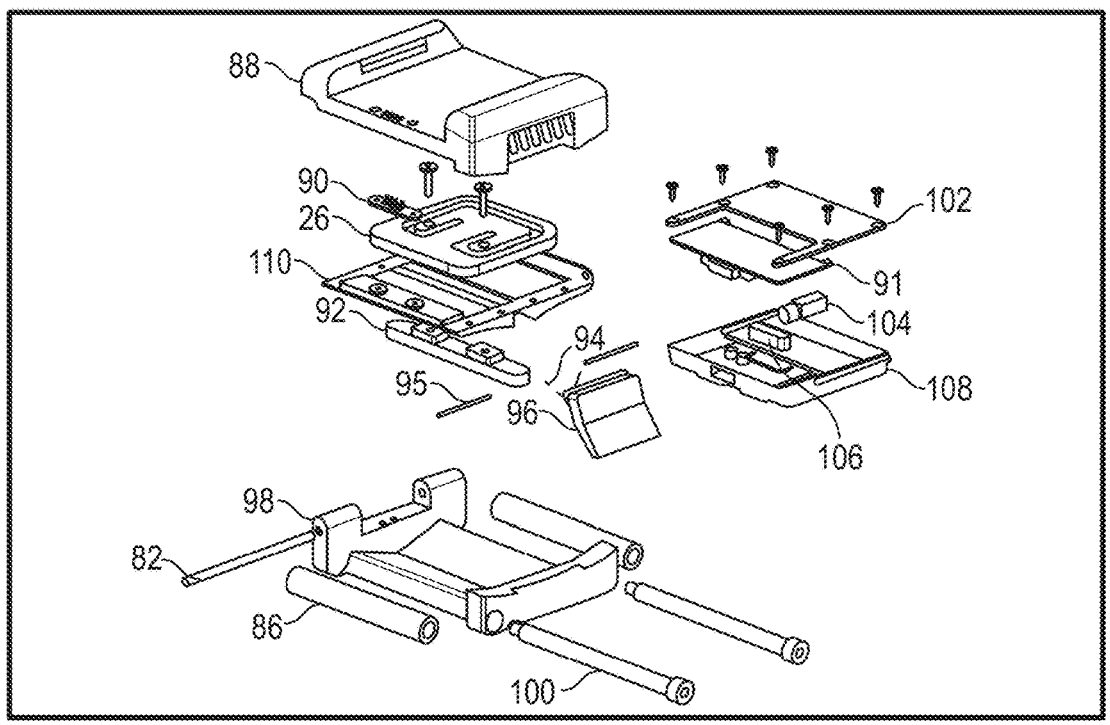
FIGS. 34 and 35 illustrate various components of an exemplification of a system employing rollers 86 and a center bar 92 to generate strain in a resistive element 18 that is detected by a strain gauge 26.
Figure 35:
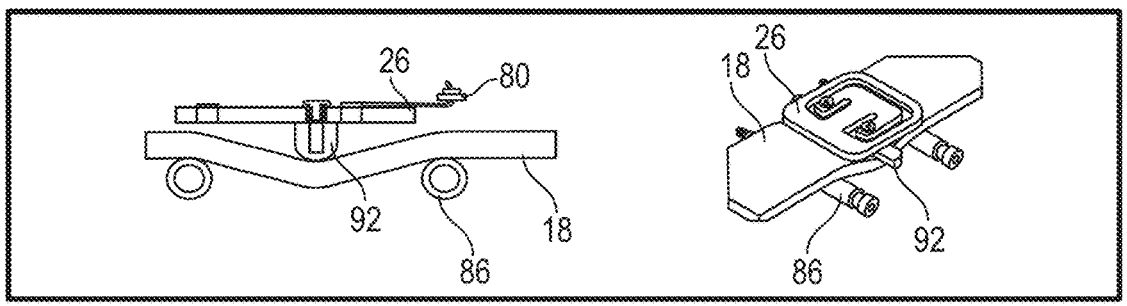

When the anchoring module 12 attaches to a resistive element 18, it changes the profile of the resistive element 18 from a straight line to a wave by using three reaction-force vectors, perpendicularly placed with respect to the resistive element 18, center bar 92 and two rollers 86 (see FIGS. 34 and 35). When a force is applied to the anchored resistive element 18, it attempts to straighten, displacing the opposing center bar 92 in the opposite direction from the rollers 86. The center bar 92 is attached to a strain gauge 26 and causes the changes in electrical resistance of the strain gauge 26 when being displaced. The higher the tension in the resistive element 18, the greater the change in electrical resistance of the strain gauge 26. The ratio between forces is not 1-to-1 and depends on the height of the center bar 92, the spacing between rollers 86 and spacing between the center bar 92 and rollers 86. The ratio doesn't depend on the width of a resistive element 18 but may change if a very-thin resistive element 18 will be used. If the proposed design will be used with an "approved" resistive element 18 of a known thickness, there is no need to perform a calibration every time before use; and the user 20 will be able to input what resistance band 18 they are using.

In the exemplification of FIG. 35, the strain gauge 26 converts applied force to a change in electrical resistance. The strain gauge 26 measures the amount of strain in a metal flexure. This component is bought off the shelf and modified to suit this context. The electronics contacts connect the strain gauge 26 to the electronics module 14 using spring-loaded contacts. The center bar 92 controls the profile of the resistive element 18 and transmits applied forces to the strain gauge 26. The rollers 86 reduce friction while causing the resistive element 18 to exert force on the center bar 92.

The offset angle determines the performance of the force-sensing mechanism. A greater offset angle produces a greater force-transfer function, meaning a greater amount of force is transferred from a resistive element onto the strain gauge 26, higher resolution, and reduction of the nonlinearity that can be caused by a resistive element 18 compressing under the high forces. A smaller offset angle results in the transfer of less force onto the gauge 26; therefore, the structural frame of the anchoring module 12 can be less stiff; closing of the mechanism can be easier for a user; and a smaller form factor (i.e., a lower height normal to the resistive element 18) of the electronics module 14.

Figure 36:
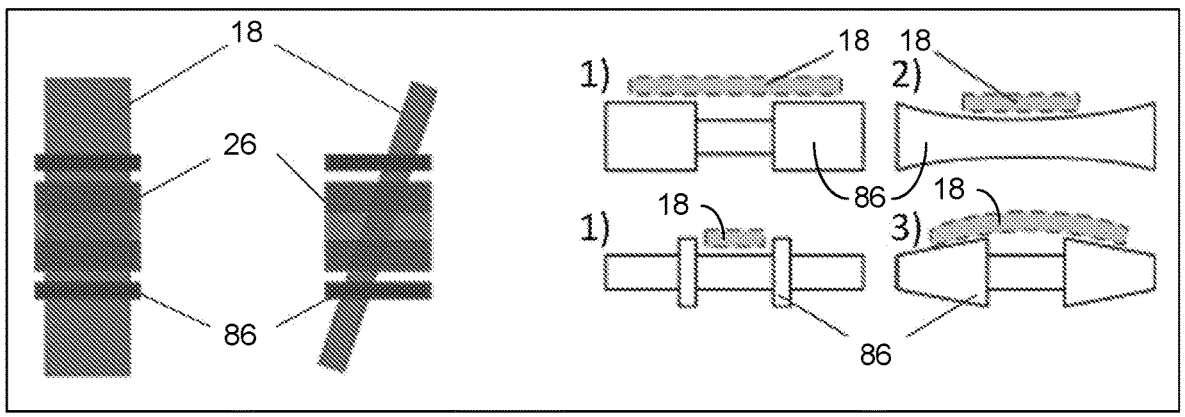
FIG. 36 shows misalignment of a resistance band 18 on rollers 86 (at right) and rollers 86 with profiles that guide a resistance band 18 to the center of the anchoring module 12.

The proposed architecture accommodates resistive elements 18 of various widths. This design introduces a challenge of narrow profiles of the resistance bands 18 not being aligned and not being centered with the rollers 86. This misalignment causes a nonlinear behavior of the force-sensing mechanism (see FIG. 36). To address this issue, the rollers 86 are designed with profiles that guide a resistance band 18 to the center of the anchoring module 12. Configuration of the profile of this design can either restrict a band 18 of a given width from shifting side to side via the use of barriers/steps, as shown in image (1), or settle a band 18 in the middle of the roller 86 with a use of concave or convex curves, as shown in image (2). A mixture of methods, shown in image (3), can be used to target bands 18 of different widths.

The following description is directed to an exemplification of the electronics module 14 that can be used with the proposed unitary one-piece anchoring module 12. Basic elements of the electric circuit of the proposed system can include the following: a microcontroller to read and process data and a Bluetooth transmitter to transmit the data to a screen; a Wheatstone bridge and an amplifier to read a change in electrical resistance when a force is applied to a resistance band; and an inertial measurement unit (IMU) to detect a user's motion in a 3D space. Optional components can be used for the user interface (inputs/outputs) and include but are not limited to light-emitting diodes (LEDs), buttons, and haptic actuators. A global-positioning-satellite (GPS) module can be used in combination with the IMU to track outdoor cardio activities.

Connection to a mobile phone can be provide provided by the Bluetooth transmitter and microcontroller. Instruments used for strength training can utilize the strain gauge and amplifier, as well as the IMU. Tracking of a cardiopulmonary workout can utilize the IMU and GPS. Basic information can be communicated to the user by the LEDs, buttons, and haptic actuator. Finally, battery life of greater than 24 hours can be provided via power management and the battery and button.

Figure 37:
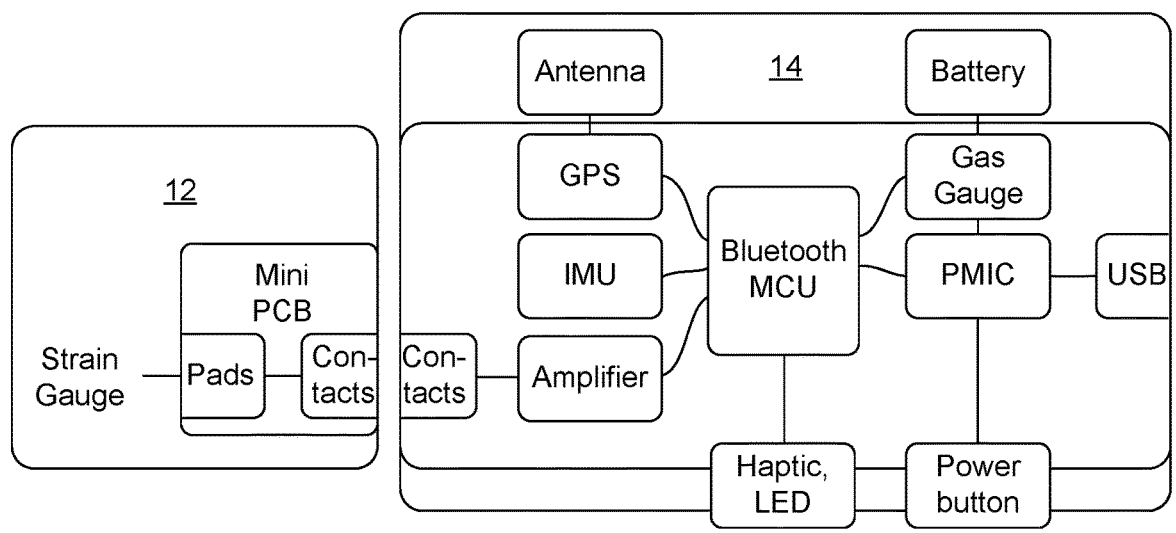
FIG. 37 schematically illustrates the architecture of an exemplification of the electrical circuit of an anchoring module 12 and electronics module 14.

The exemplification of the electrical circuit schematically shown in FIG. 37 describes the high-level architecture and logic of the anchoring module and the electronics of the electronics module. Most of the electronic components (e.g., the GPS module, the IMU, the amplifier, the haptic actuator, the LED, a gas gauge, and a PMIC) communicate directly with the microcontroller. The power circuit comprises a USB port, a battery with a gas gauge, and a power management system. While the IMU sensor and optional GPS sensor are located on the main printed circuit board in the electronics module, a force sensor (e.g., a strain gauge) is placed inside the anchoring module and engages with an amplifier in the electronics module when two modules are interlocked and connected by means of electrical connections.

The electronics module 14 has three operating modes:
Exercise: tracks a variety of the exercise metrics, described above, performs basic sensor data processing, and sends data via, e.g., a Bluetooth transmitter;
Bluetooth transmission (or communication via another protocol): pairs to an external device when an assigned button is pressed for a long time and updates firmware over the air after a normal connection is established; and
Charging: charges the battery and, optionally, shows the remaining percent of battery life via integrated outputs, such as lights or an externally connected device.

Figure 38:
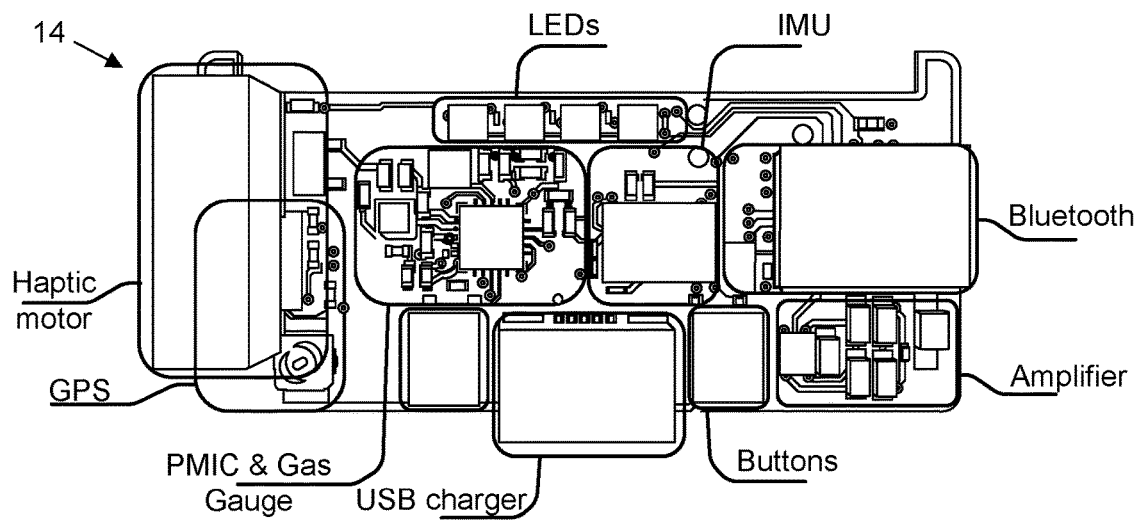
FIG. 38 illustrates an exemplification of the layout of components of an electronics module 14.

The proposed architecture can be implemented in a variety of ways with components varying in specifications, features, size, and pins lay out. FIG. 38 shows an exemplification of the layout of the components.

Figure 5:
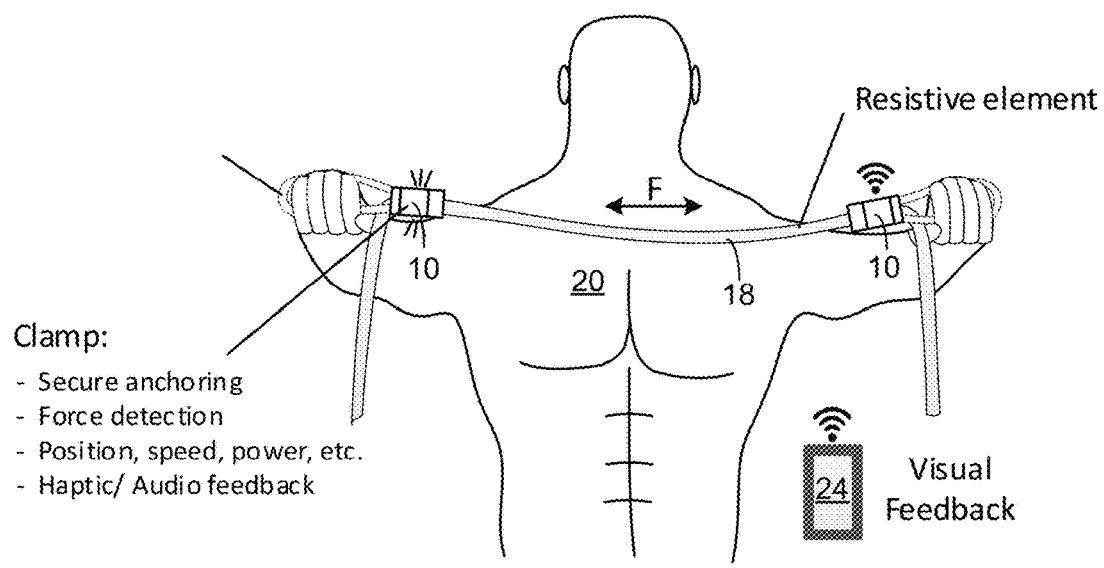
FIG. 5 shows a system configuration where two sets 10 of modules operate as clamps proximate the user's hands.

In a second exemplification, functions and features of a proposed system 10 are exemplified via a configuration in which a user stretches a resistive element 18 with both hands using two systems 10, operating as clamps, as shown in FIG. 5, which shows two systems 10, each including anchoring, electronics and interface modules. The anchoring module securely anchors to the resistive element 18 and transfers forces applied by a user from the interface module through the electronics module to the resistive element 18. The electronics module includes a force sensor that directly measures applied force. Additionally, the electronics module includes one or more sensors that allow measuring a relative distance between two sets of modules and its orientation and position in 3D space. The two systems 10 are not limited to measuring the same data or to including the same sensors or electronics. A combination of the sensors in the electronics module can gather a spectrum of information during an exercise, including applied force, amplitude and percentage of stretch, speed and acceleration of motion, orientation of the system in 3D space and trajectory of motion, and applied power.

The information collected by the system 10 is not limited to the list above. Processing and filtering of the collected data on a software level can generate a variety of additional metrics; for example, we can determine smoothness of motion, repeatability, or intensity by integrating speed, force and stretch data.

The system 10 gathers data and provides feedback to a user via communication to an output device. Feedback can include but is not limited to one or more of the following: a visual representation on a display by use of a portable or stationary PC; the use of sound from a speaker; and haptic feedback, e.g., from a piezoelectric actuator. The two systems 10 are not limited to measuring the same data or to including the same sensors or electronics.

Exemplifications of the proposed system 10 can be used with any type of resistive element 18, such as resistance bands (e.g., tubular bands; flat bands; thin bands, such as THERABAND resistance bands); and loops. The system 10 can also be used with non-extensible flexible materials, such as rope or cable in place of the resistance band. In this case, the resistive element 18 (rope or cable) will not stretch; but the system 10 will still be able to measure the applied forces.

The following discussion is directed to a third exemplification with a resemblance to the exemplification described above. This example does not illustrate the modularity feature but can include it. One can imagine how a quick release mechanism can be added to each module in this exemplification. Electronics and sensors embedded into the modules are not shown, except for the force sensor. Each function shown in this example can be implemented differently, with alternative options presented further herein.

Figure 14:
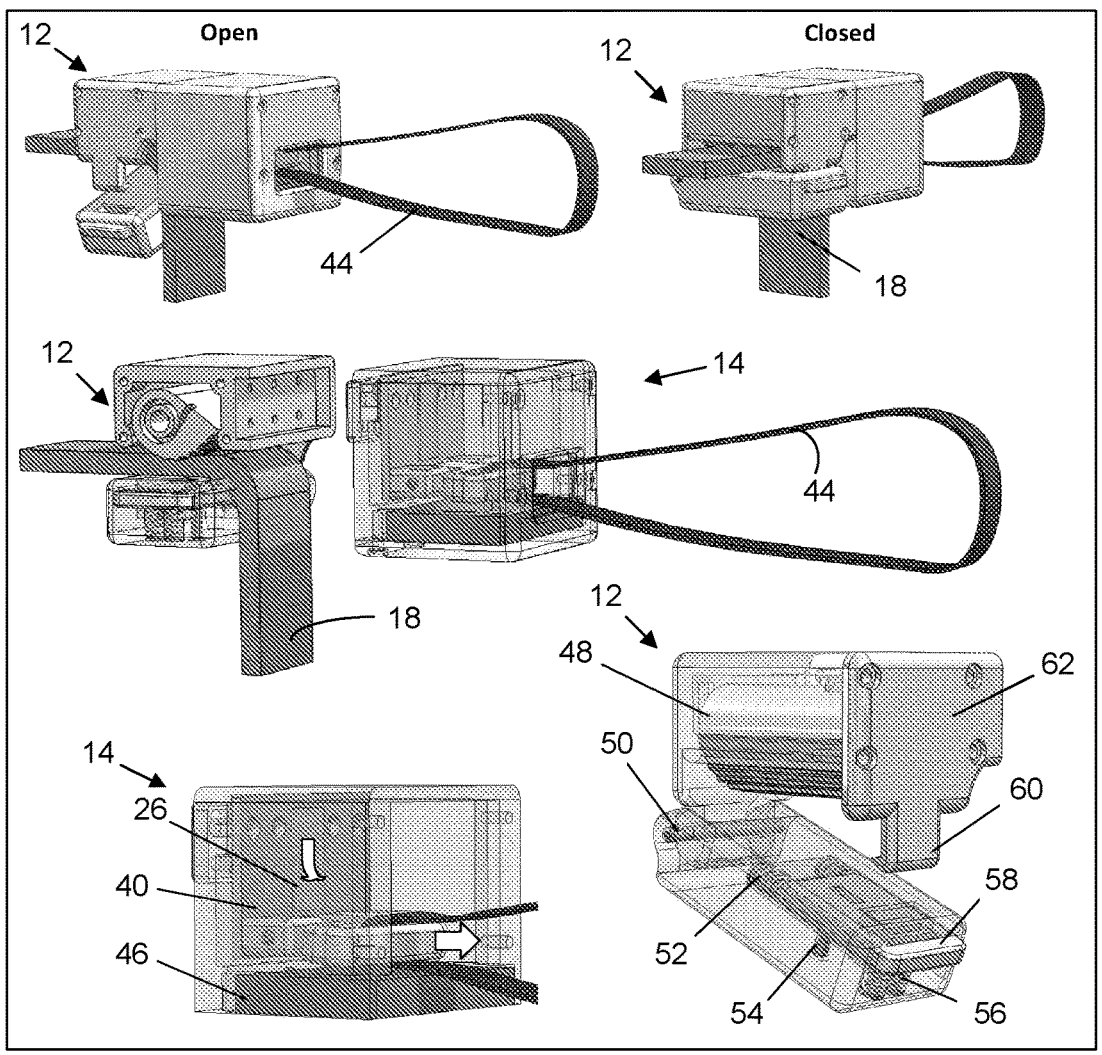
FIG. 14 shows the internal structure of an exemplification of the anchoring and electronics 12 and 14 modules in a system.

The system illustrated in FIG. 14 has two distinguishable modules (anchoring and electronics modules 12 and 14) with a strap 44 directly embedded into the electronics module 14. As mentioned earlier, the strap 44 can be a part of a separate "interface" module 16. The core mechanism of an anchoring module 12 can be in the form of a spring-loaded cam cleat that operates as a clamp 30 to secure a resistive element 18 inside the body 62 of the electronics module 14. The electronics module 14 contains a force sensor 26 implemented by a strain gauge applied onto a thick metal carrier 40 that measures bending strain. Additionally, the electronics module 14 includes, but is not limited to, the following components: a microcontroller, an amplifier, input/output (I/O) devices or ports, a Bluetooth communication transmitter/receiver, an inertial measurement unit (IMU) sensor; an accelerometer, which can be included in the IMU; a battery 46; a speaker; a power switch; light emitting diodes (LEDs); additional sensors, such as proximity, temperature, and/or vibration sensors; and a microphone.

The anchoring module 14 includes the clamp 30 that attaches to a resistive element 18. The clamp 30 can include one spring-loaded cam cleat 48, a hook 60, a push button 58, locking and releasing springs 52 and 56, a shaft 50, and a restricting pin 54. When one locks the module 14, the hook 60 contacts the button 58 and remains fixed due to the force applied by the locking springs 52. Mechanics of the locking springs 52 and the position of the restricting pin 54 determine the button's range of motion. The hook 60 is released by the releasing springs 56 when the button 58 is pushed. Once the clamp is locked, the spring-loaded cam cleat 48 restricts a resistive element 18 from slipping. The cam cleat 48 is a transmission that transforms a shear force applied in parallel to the cam cleat 48 into a normal force applied to the resistive element 18. The more force the user applies to a resistive element 18, the stronger is the grip on the resistive element 18.

As will be discussed further herein, there are multiple ways to implement a force sensor 26. In one exemplification, a strain gauge measures bending strain when force is transmitted from the interface module 16 to a resistive element 18. FIG. 14 does not depict an interface module 16, which can essentially be in the form of a strap 44 with a quick release; instead, FIG. 14 shows a strap 44 directly attached to the electronics module 14. When a user pulls on the strap 44, the strap 44 bands a metal piece (a carrier 40 in FIG. 14) with a strain gauge 26 bonded on top. The carrier 44 is grounded to the body 62 of the electronics module 14, which securely anchors to a resistive element 14 by means of the anchoring module 14.

Figure 16:
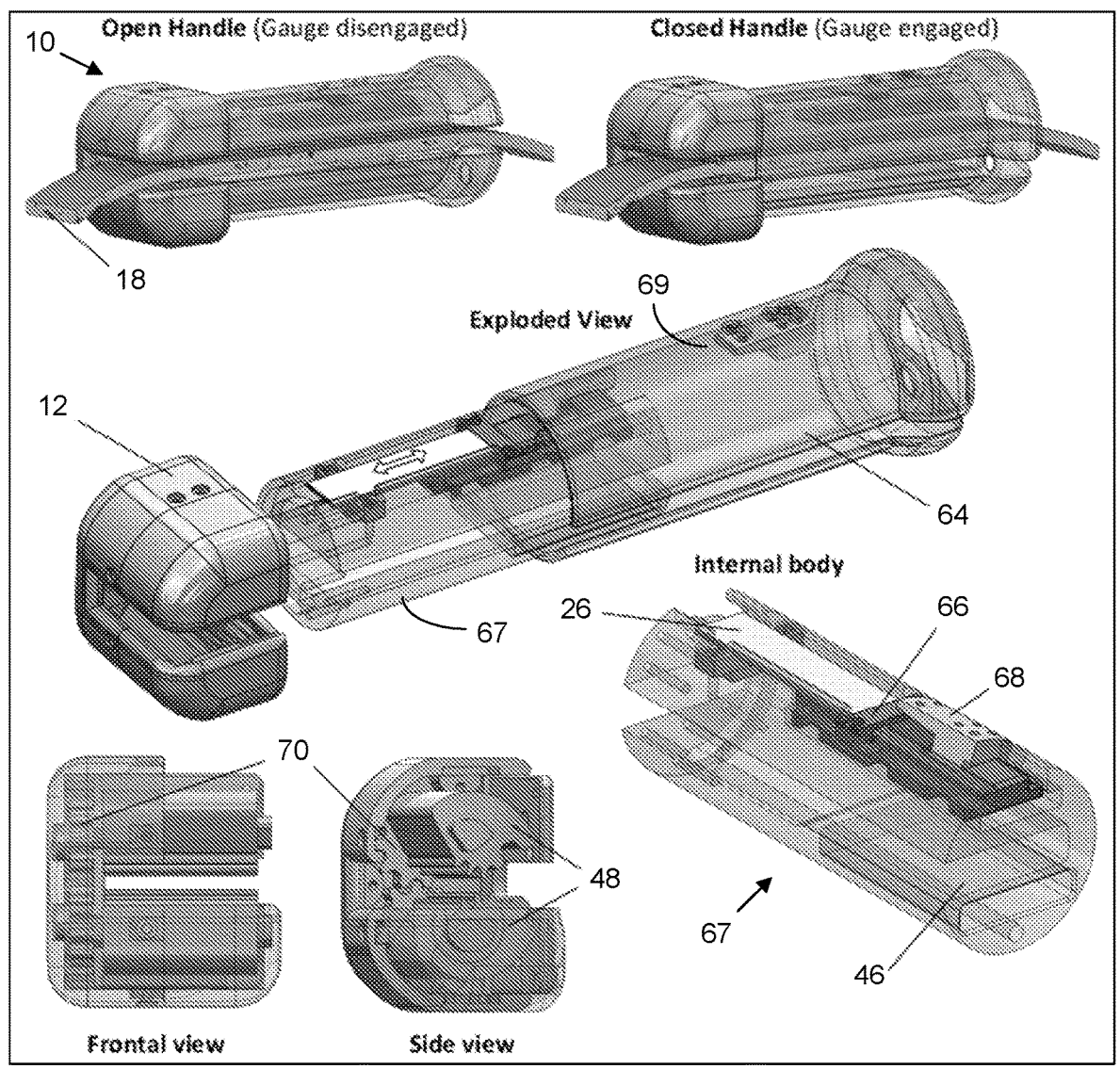
FIG. 16 is an illustration of an exemplification where the system 10 is incorporated into a rigid handle, including the internal structure of the handle.

In a fourth exemplification, the system 10 is incorporated in a rigid handle, as shown in FIG. 16. While they otherwise can be similar, differences between this embodiment and previously discussed exemplifications include the following:
the system 10 incorporated in the handle is an example of a non-modular system, as the components are not readily separable; an anchoring mechanism is permanently attached to an electronics component, and an interface handle is coaxially aligned and moves in relation to the electronics component;
an anchoring mechanism in this configuration incorporates two spring loaded claim cleats with no locking mechanism; and a force sensor 26 that is a part of the electronics component in this configuration incorporates a strain gauge applied onto a very thin metal carrier that measures an axial strain instead on bending.

The non-modular exemplification of the system 10, like previous exemplifications includes the following three main components, as shown in FIG. 16: an anchoring mechanism; an electronics component, here, in the form of an internal body 67 incorporating a strain gauge 26, electronics and a battery 46; and an interface component 69, here, in the form of a handle for a user to apply force.

The anchoring mechanism is what holds the device attached to a resistive element 18 (e.g., a band). The anchoring mechanism includes two spring-loaded cam cleats 48 and a gear 70 to synchronize motion of the cam cleats 48. The more force is applied onto the resistive element 18, the harder the cam cleats 48 squeeze, thus preventing the resistive element 18 from slipping. The anchoring mechanism can be attached to the internal body 67 by means of screws.

The internal body 67 incorporates a strain gauge 26 that measures axial strain applied by a user by means of a slider 66. One end of the strain gauge 26 is attached to the frame of the internal body 67, itself, and another end is attached to the slider 66 (FIG. 16). A user does not directly encounter the internal body 67. Instead, the user holds a sliding handle 69 that is coaxial with the internal body 67 and that has a hook 68 attached from an inner side of the handle 69. When a user applies forces to the handle 69, the hook 68 makes contact with the slider 66 and transfers forces from the user's hand to the strain gauge 26. There is not much visible displacement between the internal body 67 and the handle 69 because the strain gauge 26 has a very high tensile stiffness and, therefore, does not stretch much.

Figure 17:
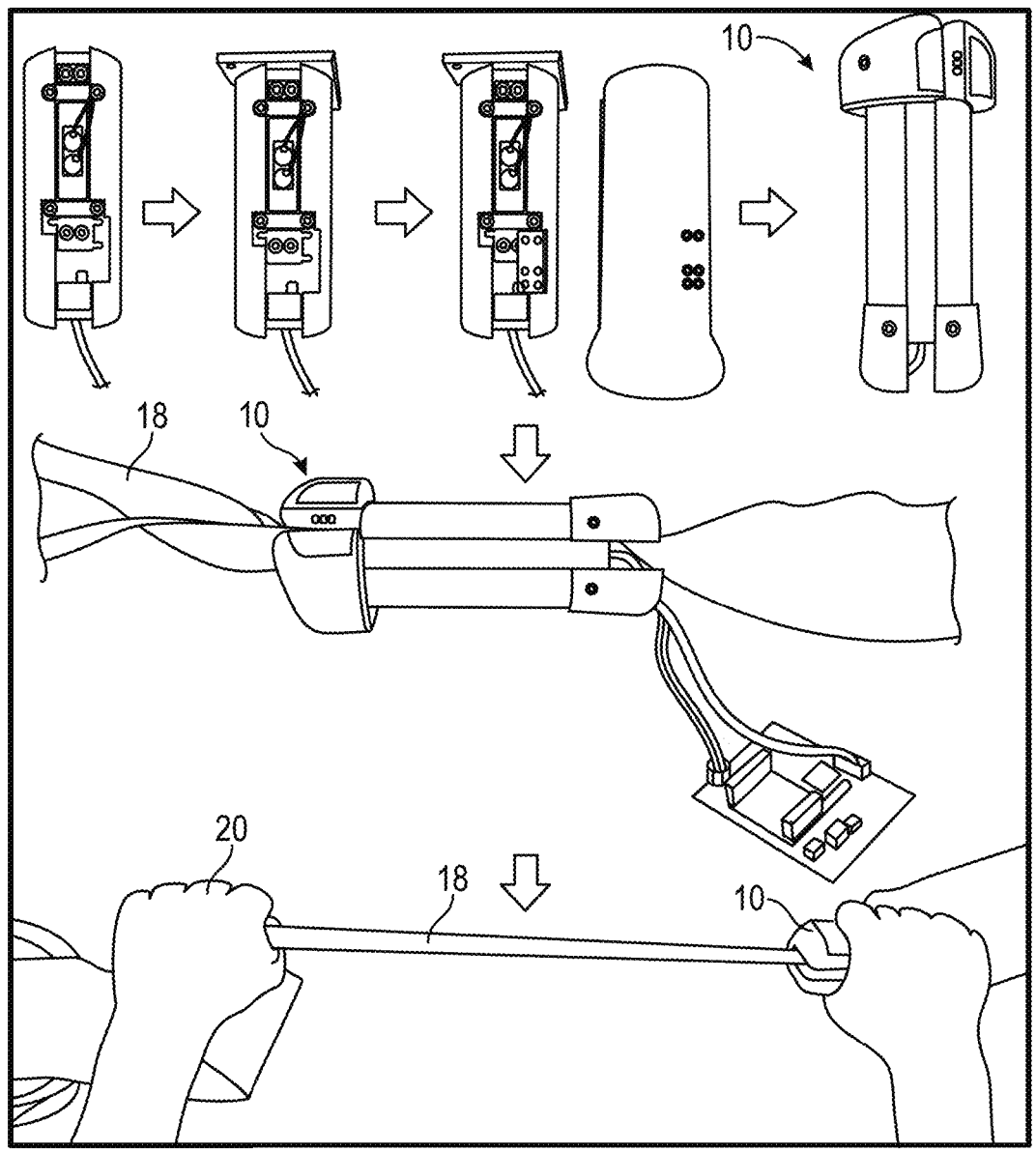
FIG. 17 includes additional images of the system 10 in the form of the rigid handle of FIG. 16.

The system can provide audio feedback to the user by means of an embedded speaker, visual feedback to the user by streaming data onto the portable PC/smartphone that provides feedback via text or images on a digital display, and/or haptic feedback by means of vibrations generated, e.g., via an eccentric rotating mass or linear resonant or piezoelectric vibration motors. Another image of a rigid handle exemplification of the system 10 is shown in FIG. 17 secured to an attached resistance band 18.

As listed above, in addition to the force sensor 26, an electronics module can include an IMU sensor to measure an orientation of the system in 3D space as well as its speed of motion. Knowing orientation and possibly a trajectory of motion helps the system to determine if a user performs an exercise in a correct form. Knowing the speed of motion enables the extraction of important metrics, such as power. In various exemplifications, the measurements of an IMU can be used to generate a spectrum of information, including the following:

- amplitude and percentage of stretch of a resistive element;
- range and/or speed and/or acceleration of motion;
- orientation of the system in 3D space and trajectory of motion;
- estimation of limb or body movement;
- estimation of user range of movement;
- repetitions during free body motions, examples of the motions are listed above;
- amount of time a user can stay in a given position, examples of the positions are listed above;
- distance moved over ground and pace of motion during walking and/or running;
- flexibility either of a single joint or of multiple joints during a complex movement;
- user's body dimensions;
- static/dynamic balance and stability;
- reaction time; and
- rest and recovery time.

The system can calculate a number of derivative metrics based on acquired force, speed, position and time. For example:

- smoothness of the exercise can be calculated by integration of applied force or speed over time;
- calories burned can be calculated by knowing the exerted force and the metabolic equivalent of the exercise;
- the index of explosiveness or rate of force development can be calculated by measuring the time within which the user reached a target force;
- repeatability can be calculated based on the consistency of the maximum values of force and/or speed data over the period of the exercise;
- intensity can be calculated by integrating speed, force and stretch data; and
- power can be calculated based on measured applied force and the speed of motion; extracting power metrics is advantageous for training and rehabilitation.

Lastly, the electronics module 14 may include additional sensors to measure the following parameters:

- the relative position of two sets of modules (e.g., the position between two clamps), which will provide knowledge of amplitude of motion and percentage of stretch;
- the temperature, which can be used to account for possible errors due to drift in electronics parameters;
- color or other properties of a resistive element that are indicative of how it will respond to force;
- sound and vibration;
- heart rate; and
- physical location and distance moved over ground via GPS.

The system 10 can provide feedback to a user 20. Feedback can include, but is not limited to, one or more of the following: audio feedback by means of an embedded speaker (e.g., in the electronics module); visual feedback by streaming data onto a portable PC/smartphone that provides feedback via text or images on a digital display; and haptic feedback by means of vibrations generated, e.g., via an eccentric rotating mass, linear resonant, or piezoelectric vibration motor.

In additional exemplifications, the system 10 can also be in communication (e.g., via a wireless transmitter in communication with a router) with the internet to share data online with, e.g., other users, a trainer, or a therapist.

Figure 6:
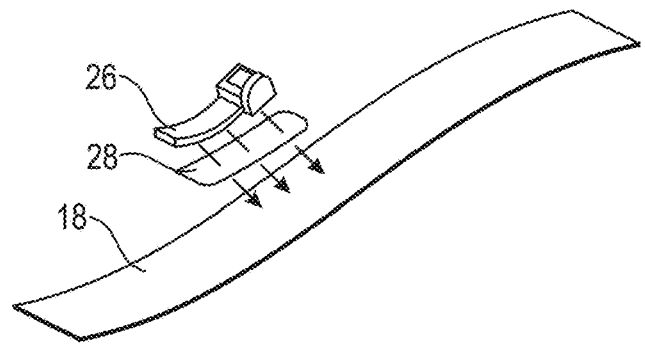
FIG. 6 is an exploded view of an electronics module, including a strain sensor 26, adhered to a resistive band 18 via adhesive 28.
Figure 7:
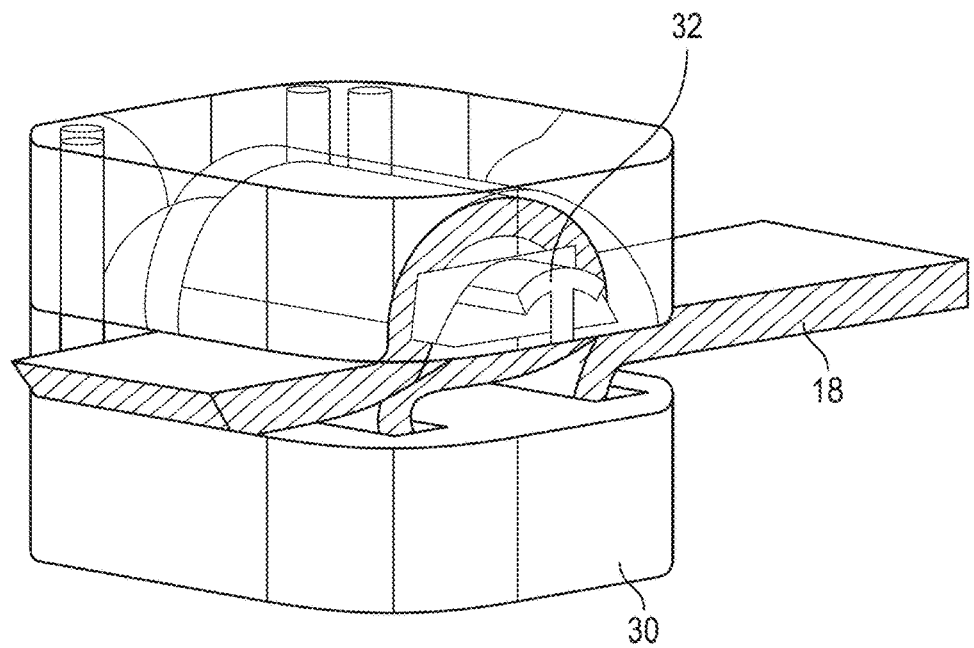
FIG. 7 shows an exemplification of a clamp 30 including a rotating shaft 32 and using friction to secure a resistive band 18.
Figure 8:
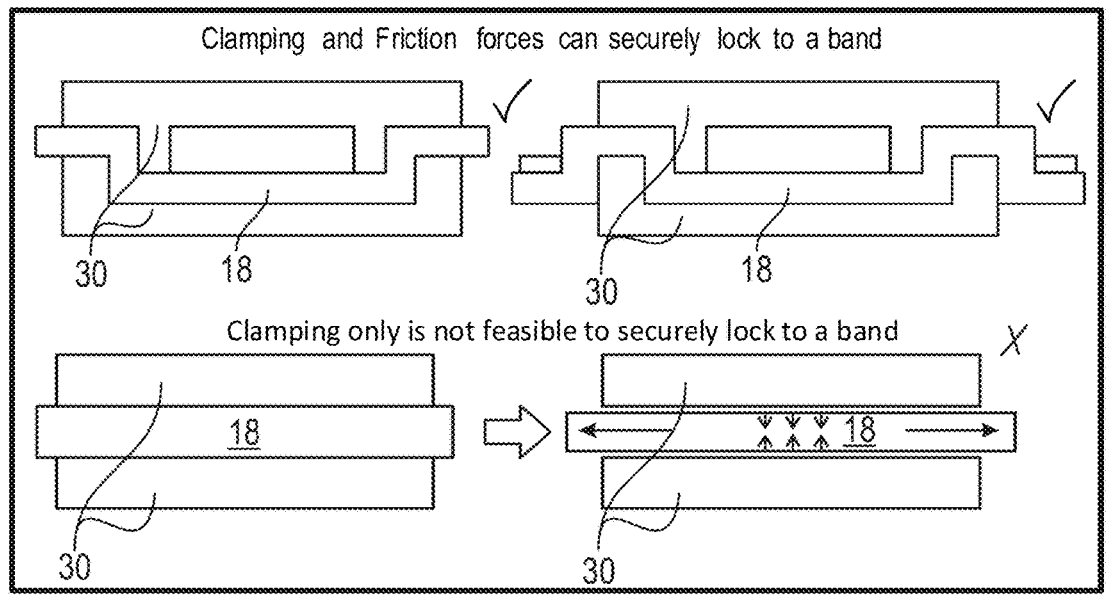
FIG. 8 shows an exemplification of a clamp 30 using a combination of clamping and friction to secure a resistive band 18.
Figure 9:
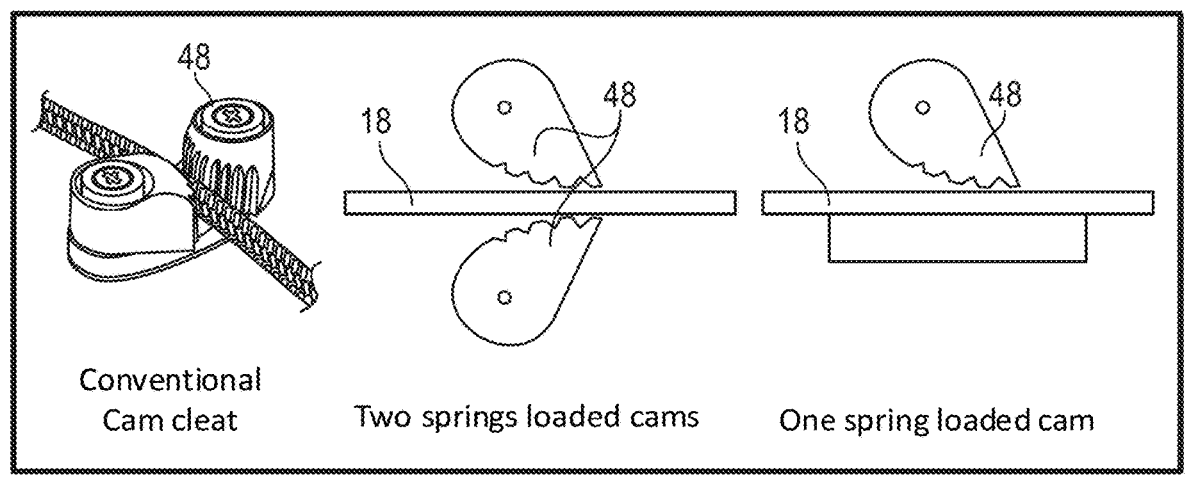
FIG. 9 shows an exemplification of a cam cleat 48 that forms a component of a clamp 30.

An anchoring mechanism can securely attach sensors and electronics to a flexible resistive element 18 (e.g., a band). The anchoring can be achieved by one or more of the following:

- adhesion—e.g., where an electronics module is glued on top of the band, as shown in FIG. 6;
- friction—e.g., where a band wraps around a rotating shaft inside a clamp, as shown in FIG. 7; a flexible band wraps around the periphery of a rotating shaft to produce a braking action; when force is applied onto the band, it causes the band to tighten around the rotating, shaft and it places the friction surfaces in contact with one another;
- clamping and friction—e.g., where a clamping mechanism is used to hold or secure objects tightly together to prevent movement or separation through the application of inward pressure, as shown in FIG. 8; even though most of the locking comes from the forces applied normally to a band, this approach also involves friction forces caused by banding the band inside the clamp; if only normal forces are applied to a band, the band will be getting thinner when stretched and eventually will slip out from a clamp; and cam cleat—a cleat is a device for securing a rope, band or other element; a cam cleat 48, as shown in FIG. 9, is a cleat in which one or two spring-loaded cams pinch the rope, band, or other element, allowing the pinched element to be easily adjusted; to anchor an electronics module to a band by using a cam cleat, either one or two spring-loaded cams can be used. In a standard cam cleat mechanism, a rope can be easily removed when under a load. In an exemplary cam-cleat mechanism, as shown at lower right in FIG. 14, removal under load is prevented, since the body 62 that incorporates a spring-loaded cam 48 securely locks a flexible resistive element 18 inside until the release button 58 is pushed, as described above.

Figure 25:
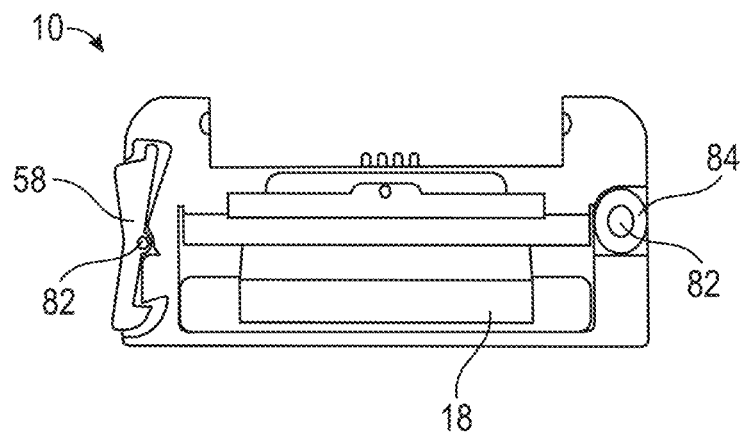
FIGS. 25 and 26 show a system 10, wherein anchoring is achieved via encapsulation.
Figure 26:
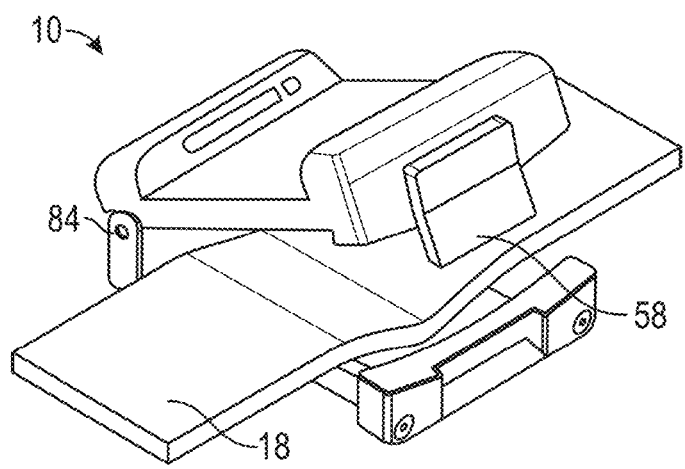
Figure 27:
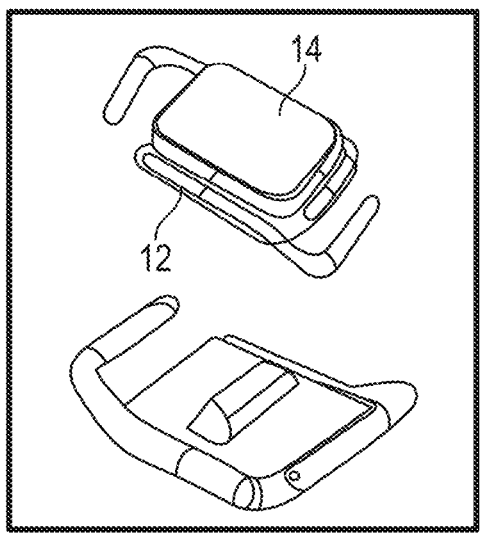
FIGS. 27 and 28 illustrate another exemplification of the system without a hinge or clasp.
Figure 28:
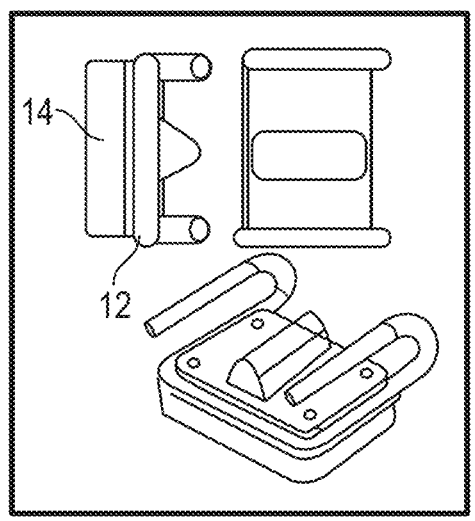
Figure 29:
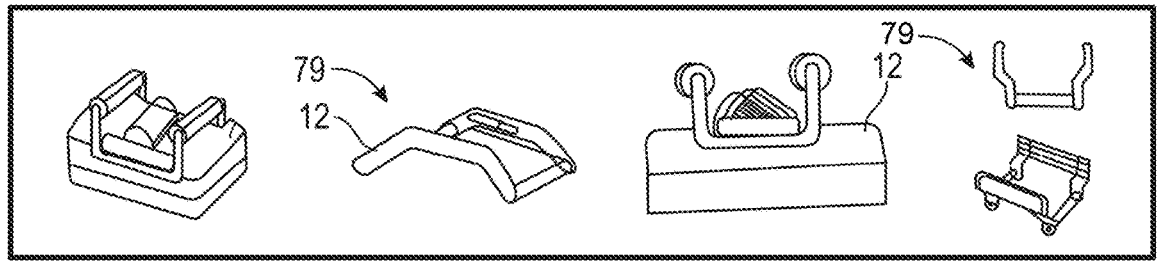
FIG. 29 illustrates a system with removable brackets 79.
Figure 30:
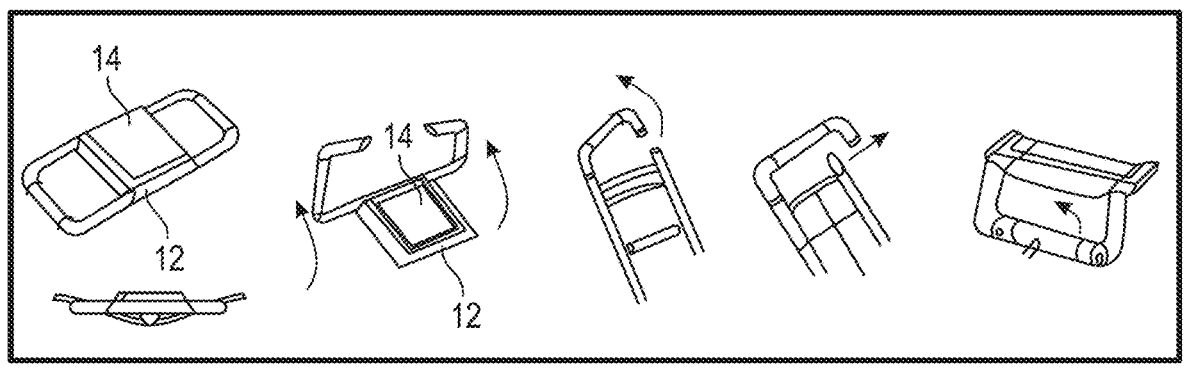
FIG. 30 shows systems with clasps 96 having a variety of rotational and sliding hinges.
Figure 31:
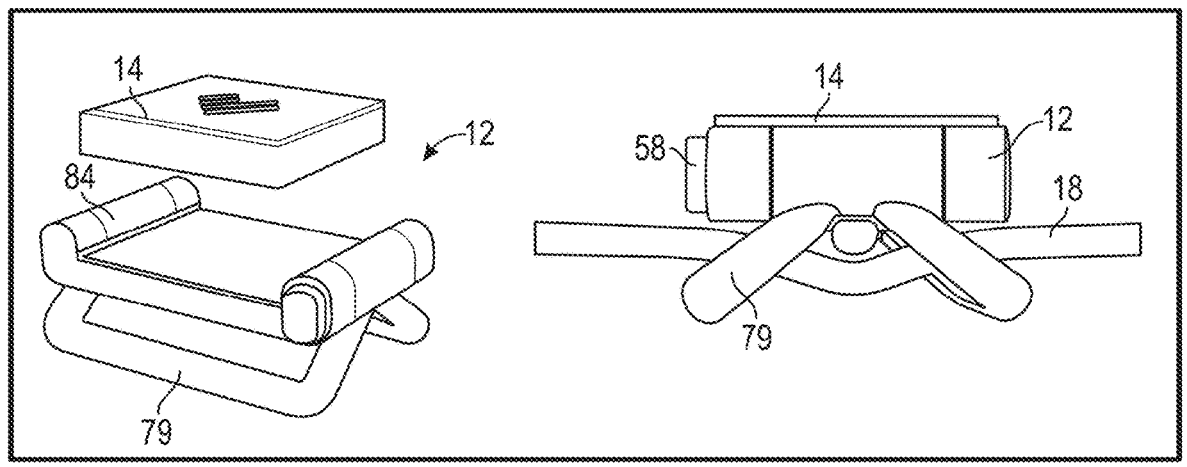
FIG. 31 illustrates a system with a bracket 79 with a rotational hinge on one side and a spring-loaded push button 58 on the opposite side.

In additional exemplifications, anchoring can be achieved via encapsulation, e.g., wherein a mechanism is used to surround a band without actually anchoring to a single point. Such a mechanism can slide along the band in either direction, though still securely hold the attached system onto a band. An example of such a system 10 is shown in FIGS. 25 and 26 and incorporates a clasp with a spring-loaded push button 58 and a hinge 84 on the opposite side of the clasp. The design utilizes preloaded torsional springs across the width of the clasp. The clasp is held in place by pins 82. Yet another exemplification, shown in FIGS. 27 and 28, includes configurations that do not involve a hinge or a clasp. In such a case, a resistive element slides into a module through a gap. The advantage of such an approach is simplicity and a reduced number of components. The clasps of FIG. 29 utilize a set of removable brackets 79, where each bracket 79 fits onto a resistive element 18 of a specific width. This configuration provides a clasping force on both sides of a bracket 79 and does not have any type of hinge. FIG. 30 illustrates clasps with a variety of rotational and sliding hinges to open and close the mechanism around a resistive element. FIG. 31 illustrates a bracket 79 with a rotational hinge 84 on one side and a spring-loaded push button 58 on the opposite side.

Modularity of the system is an advantageous feature that enables the system to be versatile. A user can apply the system to any exercise scenario with either a flexible resistive element or a constant weight, such as a dumbbell or a cable machine. Possible exercise scenarios and configurations of the modules were described above.

Any of the following three significantly different approaches can be used to measure a force applied to a flexible resistive element.

Figure 11:
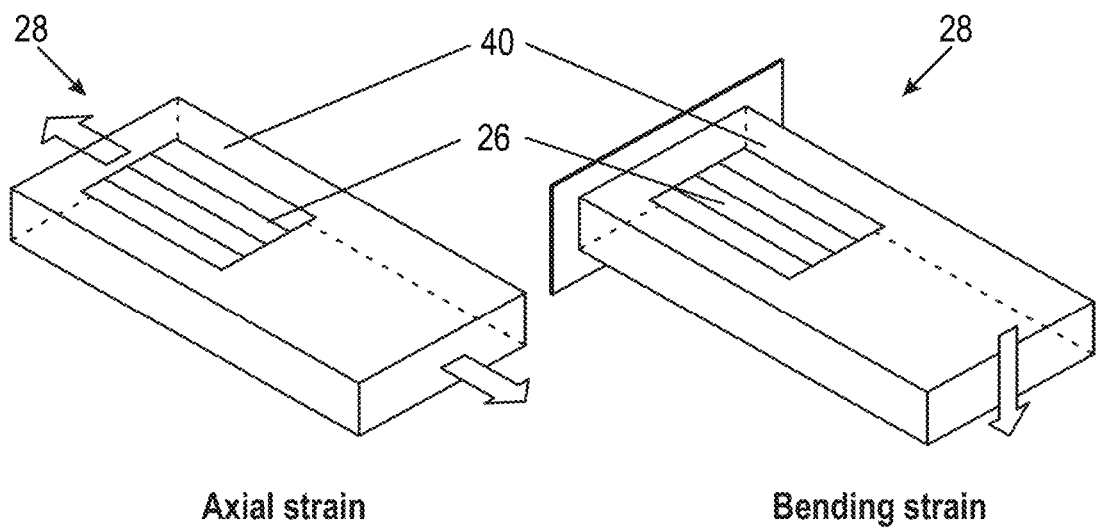
FIG. 11 shows an exemplification of a force sensor 28 with a strain gauge 26.

First, an external force sensor can be attached to a resistive element. In this embodiment, the force sensor is attached to a resistive element by means of some type of clamp. The force sensor can be a transducer that is used to create an electrical signal whose magnitude is directly proportional to the force being measured. We use a strain-gauge approach to build a force sensor; however, any of the existing force sensor techniques can alternatively be used for the force sensor to work properly. Strain-gauge electrical resistance varies in proportion to the amount of strain in the device. Material can experience either axial, bending, or shear strains; and all can be used to create a force sensor. The most widely used strain gauge is the bonded metallic strain gauge. The grid 26 is bonded to a thin backing, called the carrier 40, which is attached directly to the test specimen, as shown in FIG. 11. Therefore, the strain experienced by the test specimen is transferred directly to the strain gauge, which responds with a linear change in electrical resistance.

Second, a force sensor 26 can be incorporated as part of a resistive element 18, as shown in FIG. 6. In this case, either capacitance or resistance sensors are bonded to a high-stiffness flexible base and are attached on top of a resistive element by means of an adhesive 28 A resistive element 18 adopts the stiffness of the sensor's flexible base in the place where the force sensor 26 is glued on. When the forces are applied to a resistive element 18, they stretch the resistive element 18 as well as the flexible base of the sensor 26 of known stiffness. One can find a force applied to a resistive element 18 by measuring deformation of the flexible base by means of the capacitance or resistance sensors 18.

Third, an indirect measurement of force can be taken through deformation of the resistive element 18. Indirect measurement of force applied to two points of a resistive element 18 is possible when properties, such as stiffness, of the resistive element 18 are known. The sensors are used to measure a distance between the two points. To implement this method, either a known type of resistive element 18 can be used or the system can incorporate a sensor that can detect the type of resistive element 18 used. This detection can be realized by means of marking a resistive element 18 and using a scanner embedded in the system 10 to detect the marker and thereby determine the type of the resistive element 18. The method for measuring a distance between two points where the forces are applied is described in the following section, discussing quantification of the deformation.

Figure 12:
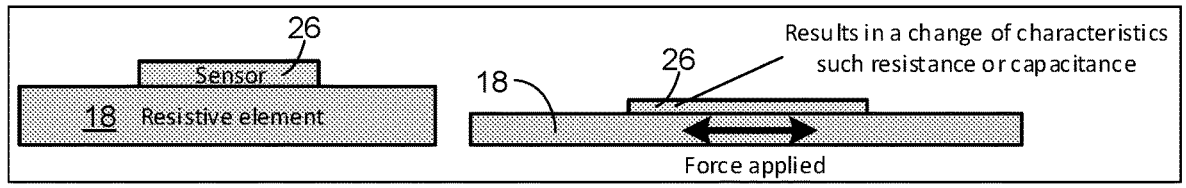
FIG. 12 shows a sensor 26 being stretched on a resistive element 18 to which it is attached and with its resistance and/or capacitance changing due to the stretching.

The stretch of the flexible resistive element 18 can be directly measured to provide quantification of the deformation. One can measure the stretch amount of the flexible resistive element 18 by means of a sensor 26 that has a stiffness lower than that of the resistive element 18. When attached to a resistive element 18, such a sensor 26 stretches the same amount as the resistive element 18, as shown in FIG. 12, and changes its output signal accordingly. If knowing the transfer function between the amount of stretch and output signal, we don't need to know the stiffness of the resistive element 18 as far as the sensor's stiffness is smaller. In many cases, the resistive elements 18 can be stretched up to 140%; and, therefore, it is an advantageous property of the sensor 26 to be able to stretch up to 140%. The principal of work of the sensor 26 can vary and is not critical for the overall system 10. The sensor 26 can work based on the change in resistance or capacitance or other characteristics.

Figure 13:
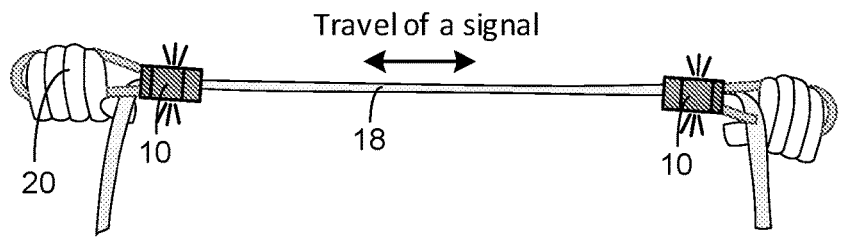
FIG. 13 shows an exemplification where the distance separating two systems 10 (and, therefore, the stretch of the resistive element 18) is measured via communication between the systems 10.

In another exemplification, the distance by which a flexible resistive element 18 deforms (stretches) can be measured by two electronics modules 14 anchored to the resistive element 18. If we assume that two sets of the system 10 are securely anchored to a resistive element 18 and that the resistive element 18 deforms between the two sets when the forces are applied (see FIG. 5), we can find the amount of stretch by knowing the distance between two electronics modules 14 of the systems 10. There are many ways to measure a distance between two electronics modules 14, with the following options representing, but not limiting, the solutions. In one example, as shown in FIG. 13, each electronics module 14 can include a wireless (e.g., Bluetooth) communication device. When sending a signal from one module to another using the communication device, we can measure how much time it takes for the signal to travel and, therefore, estimate a distance between two modules. In another example, each electronics module includes a transmitter and receiver of either light, sound or vibration to measure the time of travel and to calculate the distance of separation therefrom.

In yet another exemplification, the distance by which a flexible resistive element deforms (stretches) can be measured by an optical system. In one example, an external system can analyze the length of the band by means of visual recognition or by recognizing markers attached to a band. Another example can use a beam of light that is projected through the band itself, and the system analyzes the change of light characteristics in relation to the stretch applied.

In yet another exemplification, deformation can be measured indirectly by knowing the force applied. Indirect measurement of the deformation of the flexible resistive element is possible when properties, such as stiffness, are known; and the force sensors are used to measure a force applied between two points of anchoring. To implement this method, either a known type of resistive element can be used or a system can incorporate a sensor that can detect the type of resistive element used. This detection can be realized by marking a resistive element and using a scanner embedded in the system to detect the marking and thereby identify the type of resistive element. The method of incorporating a force sensor in the system is described in the previous section, where the quantification of the force applied is discussed.

Extracting power metrics is advantageous for training and rehabilitation, and the ability of the system to extract these metrics can be very important. The system can be used to calculate the power generated by a user if it can measure applied forces as well as the speed of motion. Either of the techniques, described above, can measure the forces. Some exemplifications incorporate the use of an externally attached force sensor. The speed of motion can be measured by incorporating an IMU sensor in the electronics module or by using a derivative of the measured deformation of the resistive element. Either of the techniques, described above, can measure the deformation of the resistive element.

Figure 15:
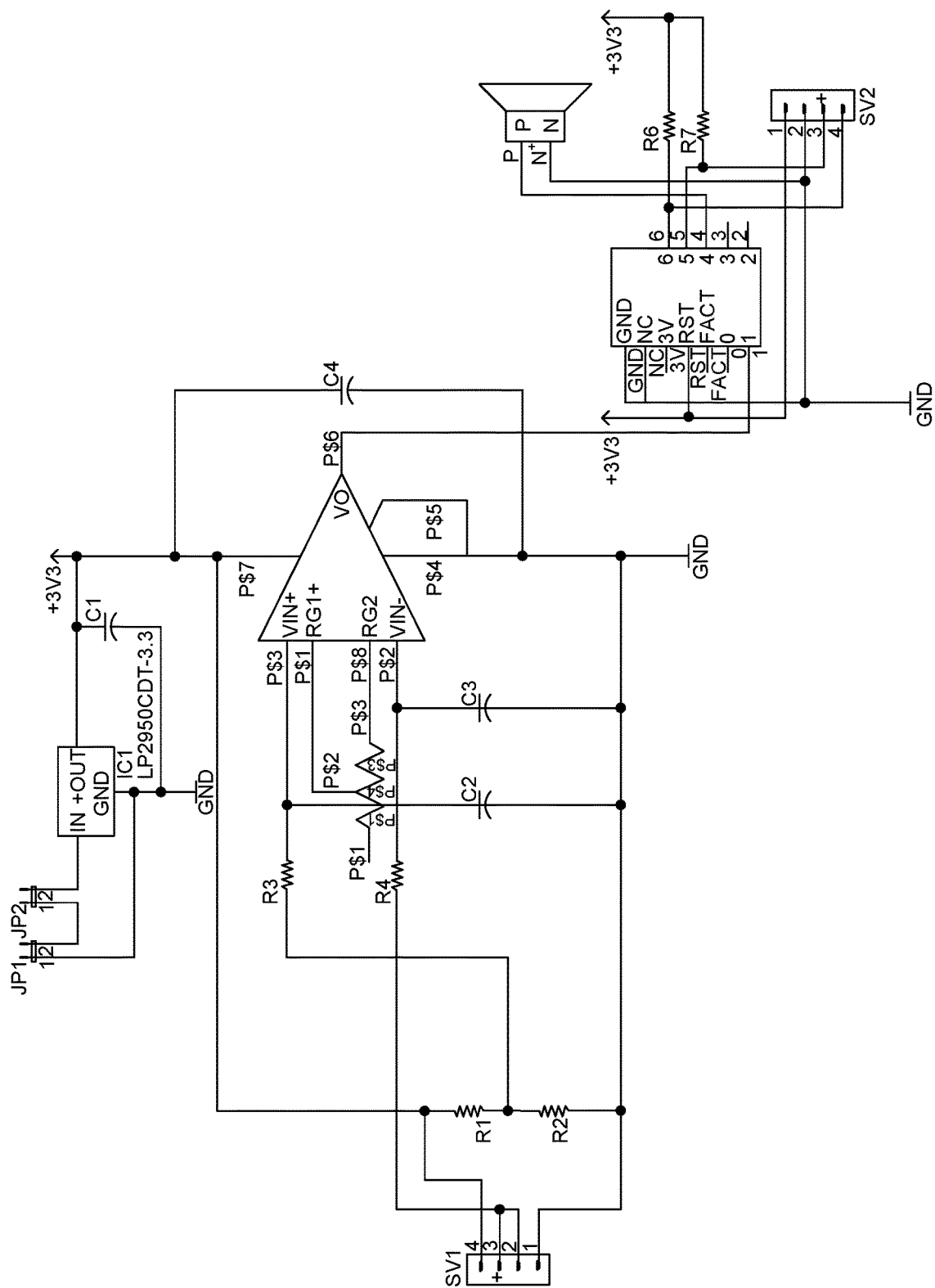
FIG. 15 is a schematic diagram of an example of an electric circuit in an electronics module.

Basic elements of the electric circuit of the proposed system include the following: a Wheatstone bridge, an amplifier, a microcontroller, a battery, and an IMU sensor. Additional elements can include, but are not limited to, a voltage regulator, a variable resistor, a temperature sensor, a speaker, a microphone, a vibration motor, a Bluetooth module, a switch, and LEDs. The exemplification schematically shown in FIG. 15, includes basic elements, a variable resistor, a speaker and a voltage regulator.

Exemplifications of Clamping Mechanisms:

In particular exemplifications, the smart resistance band architecture can involve a modular approach that allows multiple configurations of clamps, load and motion sensing modules, and handles. Although the modular approach allows for use with the broadest range of resistance band exercises, it typically requires additional time and user training to set up each exercise.

Here, we present an alternative approach that focuses on quick setup and user friendliness in a unitary one-piece configuration. The one-piece configuration can utilize a clamping mechanism designed to snap directly onto the resistance band, without the use of handles or additional modules.

Figure 18:
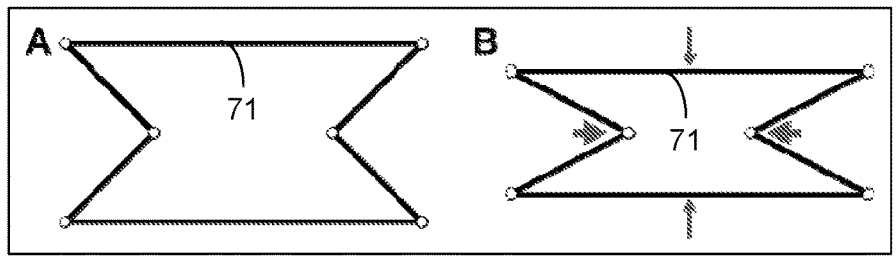
FIG. 18 is a schematic illustration of a mechanical linkage 71 used as the basis of the clamping mechanism in an open position (A) and in a closed position (B).

A mechanical linkage 71 used as the basis of the clamping mechanism is shown in FIG. 18 in an open position (A) and in a closed position (B). Circles represent revolute joints and solid lines represent rigid links. The horizontal links have additional constraints (not shown) that ensure they remain parallel and centered with respect to one another such that they can only move vertically in the orientation shown. When these horizontal links are pressed together, they produce a motion in the other links that can be leveraged to achieve the desired clamping behavior.

Figure 19:
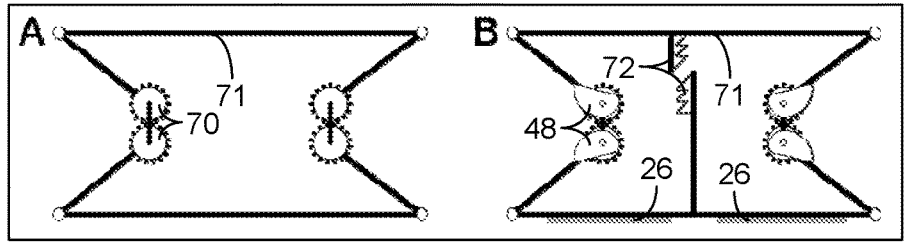
FIG. 19 is schematic illustration of the mechanical linkage 71 of FIG. 18, but with gears 70, cam-based clamping surfaces rigidly coupled to each gear 70, a ratchet-based locking mechanism 72, and strain gauges 26.

Implementation of the clamping mechanism using the linkage of FIG. 18 is shown in FIG. 19. In schematic A, the middle revolute joints are replaced with two connected gears 70. In schematic B, we further add additional components to implement the clamping functionality, including cam-based clamping surfaces coupled rigidly to each gear 70, a ratchet-based locking mechanism 72 to provide holding force after clamping, and strain gauges 26 to measure force and attached directly to the bottom link in the orientation shown. Note that the ratchet-based locking mechanism 72 may be implemented in any of a variety of ways—for example, as a linear ratchet, as shown, or integrated into one or more of the revolute joints in the linkage as a revolute ratchet and pawl. The complete device also provides means to release the locking mechanism 72 (not shown), as well as an elastic element (e.g., a spring) to return the linkage 71 to the fully open position (not shown).

Figure 20:
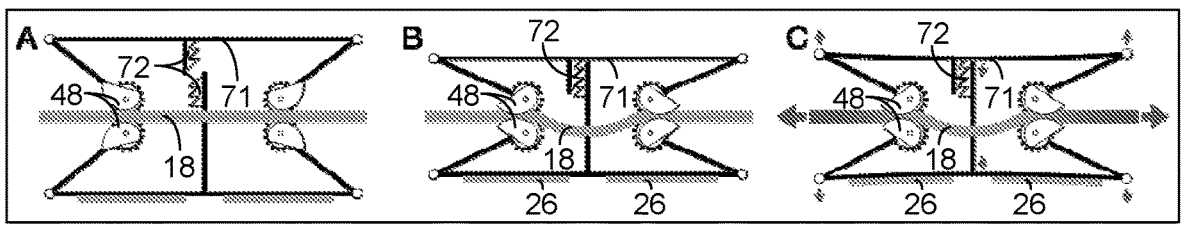
FIG. 20 shows the operating principled principle of the clamping mechanism of FIG. 19 on a resistance band 18.

The operating principles of this clamping mechanism on a resistance band 18 is are shown in FIG. 20. In A, the user inserts the resistance band 18 between the open clamping surfaces of the locking cams 48. In B, the user applies pressure to the top and bottom horizontal links, compressing the linkage 71, where the linkage kinematics cause the cams 48 to simultaneously rotate, which simultaneously clamps the resistance band 18 in two places and produces slack in the middle part of the band 18 by moving the two clamps closer together. In C, the user performs the resistance band exercise by pulling on the two protruding ends of the resistance band 18, which produces strain in the horizontal rigid links, which can then be quantified using the strain gauges 26.

The locking mechanism 72 retains this geometry until the exercise is over. The location of the locking mechanism 72 in combination with the linkage kinematics may further be exploited to provide an advantageous location for the strain gauges 26 used to quantify force applied to the resistance band 18 throughout the exercise. In C, the horizontal links have some degree of compliance relative to the other links, which introduces a strain when the two ends of the resistance band 18 are pulled. Moreover, due to the properties of the linkage 71, strain in the resistance band 18 produces amplified strain in the location of the gauges 26, increasing measurement fidelity.

This configuration can confer the following advantages:
- the one-degree-of-freedom motion of this clamping mechanism simultaneously clamps the resistance band 18 and introduces slack inside the device, enabling measurement;
- this configuration simplifies and streamlines the user experience—i.e., the user may hold the device in one hand, insert the resistance band with the other hand, and immediately actuate the clamp by squeezing the device together;
- the short (angled) links confer a lever arm advantage to the clamping cams 48, facilitating the clamping process;
- through appropriate cam design, the device can have the variable capacity to clamp onto any of the resistance bands currently on the market, regardless of band thickness;
- the device may be used with loop-style resistance bands without cutting the band; and the properties of the linkage 71 can be further exploited by integrating the strain gauges 26 directly into the linkage 71.

Figure 21:
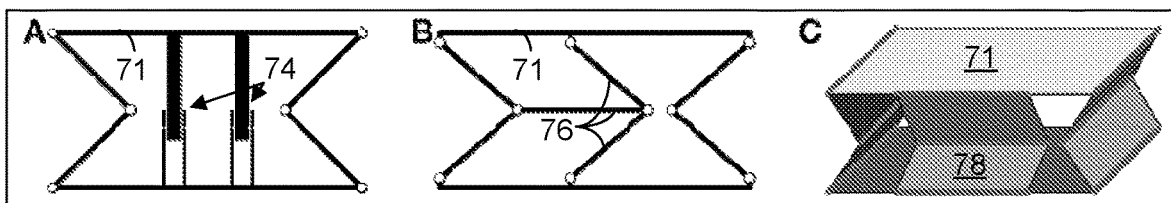
FIG. 21 shows three exemplifications of an auxiliary mechanism that constrains the horizontal links in the mechanical linkage shown in FIGS. 18-20 to always remain parallel and to only move vertically (in the orientation shown).

Constraining the horizontal links may be needed for the linkage 71 to generate the required kinematics. Three embodiments of an auxiliary mechanism that can constrain the horizontal links of this configuration to always remain parallel while only moving vertically (in the orientation shown) are shown in FIG. 21: linear sliding bearings 74 (A), an auxiliary parallelogram linkage 76 (B), and an auxiliary Sarrus linkage 78 (C).

Additional examples consistent with the present teachings are set out in the following numbered clauses:

1. A system for quantification of exercise and physical therapy, comprising:
   a plurality of modules, including:
   an anchoring module removably attached to an object (e.g., a flexible resistive band) or equipped with a clamping mechanism for removably securing the anchoring module to the object, wherein the anchoring module includes an anchoring-module coupling fixture; and
   an electronics module including:
   i. a processor configured to receive signals from a sensor (e.g., a force sensor);
   ii. a computer storage medium storing software code and in communication with the processor, wherein the software code includes instruction for processing the signals from the sensor to quantify a user's exercise or physical therapy, which may include calculating force; and
   iii. at least one electronics-module coupling fixture configured to secure the electronics module to the anchoring module coupling fixture,
   wherein at least one of the modules includes a sensor configured to generate a signal representative of the user's performance during the exercise or physical therapy, which may include exertion of force.
2. The system of clause 1, wherein the sensor includes a displacement sensor configured to generate a signal representative of displacement of the system, wherein the processor is configured to receive signals from the displacement sensor, wherein the computer storage medium is in communication with the processor, and wherein the software code further includes instruction for processing the signals from the displacement sensor to calculate displacement.
3. The system of clause 1 or 2, further comprising at least one additional sensor in at least one of the modules, wherein the additional sensor is selected from a proximity sensor, a GPS sensor, an ultrasound sensor, a light sensor, a temperature sensor, a vibration sensor, a color sensor, and a microphone.
4. The system of any of clauses 1-3, wherein the clamping mechanism is in the form of a spring-loaded cam cleat.
5. The system of any of clauses 1-4, further comprising an interface module configured for attachment to the user or to a fixture, wherein the interface module includes an interface module coupling fixture.
6. The system of clause 5, wherein the coupling fixtures are configured so that either the anchoring module or the interface module can be secured to any of the other coupling fixtures.
7. The system of clause 5 or 6, wherein the system includes a plurality of the interface modules.
8. The system of any of clauses 1-7, wherein the system includes a plurality of the anchoring modules.
9. The system of any of clauses 1-8, wherein the system comprises a plurality of the electronics modules.
10. The system of clause 9, wherein the object is a flexible resistance band, wherein a first of the electronics modules is coupled with a first of the anchoring modules secured to the flexible resistance band, and wherein a second of the electronics modules is coupled with a second of the anchoring modules secured to the flexible resistance band, and wherein the anchoring modules are respectively secured at spaced-apart positions to the flexible resistance band.
11. The system of clause 10, wherein the electronics modules include a transmitter and receiver for transmitting a signal between the electronics modules, wherein the transmitter and receiver are coupled with the processor, and wherein the software code includes instructions for measuring the time the signal travels from the transmitter to the receiver and calculates the distance between the electronics modules from that time measurement.
12. The system of any of clauses 9-11 in combination with clause 8, wherein a first of the anchoring modules is removably secured to a first of the electronics-module coupling fixtures, and wherein a second of the anchoring modules is removably secured to a second of the electronics-module coupling fixtures.
13. The system of clause 12, wherein the flexible resistance band is secured to each of the anchoring modules via the clamping mechanism in each anchoring module.
14. The system of any of clauses 1-13, wherein anchoring to the flexible resistance band is achieved by temporary or permanent adhesive.
15. The system of any of clauses 1-14, wherein the electronics module further comprises a wireless transmitter configured to wirelessly communicate with an electronics device that includes a display for visually displaying information based on information received from the wireless transmitter.
16. The system of any of clauses 1-15, wherein the electronics module further comprises a battery or a chamber configured for mounting a battery and configured to supply power to at least one component in the electronics module.
17. The system of any of clauses 1-16, further comprising an inertial measurement unit that includes an accelerometer and that also detects the orientation of the electronics module.
18. The system of any of clauses 1-17, wherein the object is a flexible resistance band, and wherein the clamping mechanism is configured to secure the flexible resistance band via a combination of clamping force and friction.
19. The system of any of clauses 1-18, wherein the clamping mechanism includes a quick-release mechanism.
20. The system of any of clauses 1-19, wherein the anchoring module is secured to a constant weight.
21. The system of any of clauses 1-20, wherein the anchoring module is secured to a cable-driven exercise machine or secured to a cable fed through the cable-driven exercise machine.
22. The system of any of clauses 1-21, wherein the sensor includes a force sensor configured to generate a signal representative of an applied force.
22.1. The system of clause 22, wherein the force sensor is implemented as one of the following: a strain gauge; a capacitance-based sensor; a resistance-based sensor; a piezoelectric sensor; and a light sensor.

23. The system of any of clauses 1-22, wherein the sensor includes a displacement sensor, wherein the displacement sensor is implemented by at least one of the following: a capacitance-based sensor; a resistance-based sensor; a light sensor; and a transmitter and a receiver coupled with the processor, and wherein the software code includes instructions for measuring the time a signal travels from the transmitter to the receiver and calculates the distance.

24. The system of any of clauses 1-23, wherein the object is secured by the clamping mechanism of the anchoring module, and wherein the object is a flexible resistance band.

25. The system of clause 24, wherein the electronics module further comprises a sensor configured to detect a marking on the flexible resistance band to identify characteristics of the flexible resistance band.

26. The system of clause 24 or 25, wherein the sensor includes a force sensor, and wherein the force sensor is anchored to the flexible resistance band in such a way that places the force sensor mechanically in series with the force input applied to the flexible resistance band by the user.

27. The system of any of clauses 24-26, wherein the anchoring module is configured to clamp simultaneously to two separate locations on the flexible resistance band.

28. The system of clause 27, wherein the anchoring module introduces slack between the two separate points of attachment to the flexible resistance band.

29. The system of any of clauses 24-28, wherein the anchoring module is configured to be actuated through a single degree-of-freedom motion.

29.1. The method of clause 24, wherein the anchoring module further comprises rollers positioned to transmit applied forces on the flexible resistive band to the force sensor.

30. The system of any of clauses 1-29, further comprising an interface module discrete from the electronics module and configured for attachment to a user or to a fixture and to the electronics module.

31. The system of any of clauses 24-30, wherein the anchoring module further comprises rollers positioned to transmit applied forces on the flexible resistive band to the force sensor.

32. The system of clause 31, wherein the rollers have a profile that serves to guide the flexible resistive band to centers of the rollers.

33. The system of any of clauses 24-32, wherein the clamping mechanism of the anchoring module further comprises a rotational or sliding hinge configured to removably secure the flexible resistive band.

33.1. The system of any of clauses 1-33, wherein the electronics module further comprises a wireless transmitter configured to wirelessly communicate with an electronics device that includes a display for visually displaying information based on information received from the wireless transmitter.

33.2. The system of any of clauses 1-33.1, wherein the electronics module further comprises a wireless transmitter configured to wirelessly communicate with the internet to store data and or share online with, e.g., other users, a trainer, or a therapist.

34. A system for quantification of exercise and physical therapy, comprising:

a plurality of modules, including:
an anchoring module, including a clamping mechanism that includes at least one spring-loaded cam cleat configured for removably securing the anchoring module to an object; and
an electronics module including:
i. a processor configured to receive signals from a sensor; and
ii. a computer storage medium storing software code and in communication with the processor, wherein the software code includes instruction for processing the signals from the sensor to quantify a user's exercise or physical therapy,
wherein at least one of the modules includes the sensor, wherein the sensor is configured to generate a signal representative of the user's performance during the exercise or physical therapy, and wherein the anchoring module extends from or is configured for attachment to the electronics module.

35. The system of clause 34, wherein the electronics module further comprises a displacement sensor configured to generate a signal representative of displacement of the system, wherein the processor is configured to receive signals from the displacement sensor, and wherein the computer storage medium is in communication with the processor, and wherein the software code includes instruction for processing the signals from the displacement sensors to calculate displacement.

36. A method for quantification of exercise and physical therapy using a system for quantification of exercise and physical therapy, comprising:
a plurality of modules, including:
an anchoring module equipped with a clamping mechanism and including an anchoring-module coupling fixture; and
an electronics module including:
i. a processor configured to receive signals from a sensor; and
ii. a computer storage medium storing software code and in communication with the processor, wherein the software code includes instruction for processing the signals from the sensor to quantify a user's exercise or physical therapy; and
at least one electronics-module coupling fixture configured to secure the electronics module to the anchoring module coupling fixture, wherein at least one of the modules includes the sensor, wherein the sensor is configured to generate a signal representative of the user's performance during the exercise or physical therapy, the method comprising:
securing the anchoring module to an object using the clamping mechanism of the anchoring module;
applying a force to the object via performance of the exercise or physical therapy;
using the sensor to quantify the performance of exercise or physical therapy; and
displaying a representation of the performance quantification.

37. The method of clause 36, wherein the method further comprises:
using the displacement sensor to measure the displacement of the system; and
displaying a representation of the displacement.

38. The method of clause 36 or 37, wherein the system further comprises a displacement sensor included in at least one of the modules, and wherein the method further comprises:
- deriving metrics selected from energy, power, smoothness of exercise motion, symmetry of the exercise motion, and other derivatives of data communicated by at least one sensor from the communicated data; and
- displaying a representation of the derived metrics.

39. The method of clause 38, wherein at least one of the metrics is represented by visual, audible, or haptic feedback.

40. The method of any of clauses 36-39, wherein the system and data therefrom are used as an input and/or control device for games.

41. The method of any of clauses 36-40, wherein the system and data therefrom are used to provide coaching feedback or to guide workouts.

41.1. The method of any of clauses 36-41, wherein the sensor is a force sensor, and wherein the force sensor measures force applied to the object.

42. The method of any of clauses 36-41.1, further comprising using the measurements of applied force to track strength, cardiopulmonary, flexibility or strength exercises.

43. The method of clause 41.1 or 42, wherein the object is a flexible resistive element, wherein the anchoring module includes at least two rollers and an opposing center bar, the method further comprising:
- generating at least three reaction-force vectors with the rollers and the opposing center bar on the flexible resistive element;
- transmitting the reaction-force vector from the center bar to the force sensor; and
- measuring the reaction-force vector transmitted to the center bar to determine tensile force in the flexible resistive element.

44. The method of any of clauses 36-43, wherein at least one of the modules also includes an inertial measurement unit, the measurement further comprising using the inertial measurement to measure at least one of the following:
- amplitude and percentage of stretch of a resistive element;
- at least one of range, speed, and acceleration of motion;
- orientation of the system in 3D space and trajectory of motion;
- estimation of limb or body movement;
- estimation of user range of movement;
- repetitions during free-body motions;
- amount of time a user can stay in a given position;
- distance moved over ground and pace of motion during walking and/or running;
- flexibility of at least one joint during a complex movement;
- a user's body dimensions;
- static or dynamic balance and stability;
- reaction time; and
- rest and recovery time.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step. Likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions, and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety for all purposes; and all appropriate combinations of embodiments, features, characterizations, and methods from these references and the present disclosure may be included in embodiments of this invention. Still further, the components and steps identified in the Background section are integral to this disclosure and can be used in conjunction with or substituted for components and steps described elsewhere in the disclosure within the scope of the invention. In method claims (or where methods are elsewhere recited), where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A system for quantification of exercise and physical therapy, comprising:
   a plurality of modules, including:
      at least a first and a second anchoring module removably secured at respective spaced-apart positions to a flexible resistance band, wherein each anchoring module includes an anchoring-module coupling fixture; and
      an electronics module including:
         i. a processor configured to receive signals from a sensor;
         ii. a computer storage medium storing software code and in communication with the processor, wherein the software code includes instruction for processing the signals from the sensor to quantify a user's exercise or physical therapy; and
         iii. at least one electronics-module coupling fixture configured to secure the electronics module to the anchoring module coupling fixture, wherein the electronics module is coupled with the first or second anchoring module or both anchoring modules,
      wherein at least one of the modules includes the sensor, wherein the sensor is configured to generate a signal representative of the user's performance during the exercise or physical therapy.

2. The system of claim 1, wherein the sensor includes a displacement sensor configured to generate a signal representative of displacement of the system, wherein the processor is configured to receive signals from the displacement sensor, wherein the computer storage medium is in communication with the processor, and wherein the software code further includes instruction for processing the signals from the displacement sensor to calculate displacement.

3. The system of claim 2, further comprising at least one additional sensor in at least one of the modules, wherein the additional sensor is selected from a proximity sensor, a GPS sensor, an ultrasound sensor, a light sensor, a temperature sensor, a vibration sensor, a color sensor, and a microphone.

4. The system of claim 1, wherein the anchoring module is equipped with a clamping mechanism that removably secures the anchoring module to the flexible resistance band.

5. The system of claim 1, further comprising an interface module configured for attachment to the user or to a fixture, wherein the interface module includes an interface module coupling fixture.

6. The system of claim 5, wherein the coupling fixtures are configured so that either the anchoring module or the interface module can be secured to any of the other coupling fixtures.

7. The system of claim 5, wherein the system includes a plurality of the interface modules.

8. The system of claim 1, wherein the system comprises a plurality of the electronics modules.

9. The system of claim 8, wherein a first of the electronics modules is coupled with a first of the anchoring modules secured to the flexible resistance band, and wherein a second of the electronics modules is coupled with a second of the anchoring modules secured to the flexible resistance band.

10. The system of claim 9, wherein the electronics modules include a transmitter and receiver for transmitting a signal between the electronics modules, wherein the transmitter and receiver are coupled with the processor, and wherein the software code includes instructions for measuring the time the signal travels from the transmitter to the receiver and calculates the distance between the electronics modules from that time measurement.

11. The system of claim 4, wherein a first of the anchoring modules is removably secured to a first of the electronics-module coupling fixtures, and wherein a second of the anchoring modules is removably secured to a second of the electronics-module coupling fixtures.

12. The system of claim 1, wherein the electronics module further comprises a wireless transmitter configured to wirelessly communicate with an electronics device that includes a display for visually displaying information based on information received from the wireless transmitter.

13. The system of claim 1, wherein the electronics module further comprises a battery or a chamber configured for mounting a battery and configured to supply power to at least one component in the electronics module.

14. The system of claim 1, further comprising an inertial measurement unit that includes an accelerometer and that also detects the orientation of the electronics module.

15. The system of claim 4, wherein the clamping mechanism is configured to secure the flexible resistance band via a combination of clamping force and friction.

16. The system of claim 4, wherein the clamping mechanism includes a quick-release mechanism.

17. The system of claim 1, wherein the sensor includes a force sensor configured to generate a signal representative of an applied force.

18. The system of claim 17, wherein the force sensor is implemented as one of the following: a strain gauge; a capacitance-based sensor; a resistance-based sensor; a piezoelectric sensor; and a light sensor.

19. The system of claim 1, wherein the sensor includes a displacement sensor, wherein the displacement sensor is implemented by at least one of the following: a capacitance-based sensor; a resistance-based sensor; a light sensor; and a transmitter and a receiver coupled with the processor, and wherein the software code includes instructions for measuring the time a signal travels from the transmitter to the receiver and calculates the distance.

20. The system of claim 4, wherein the electronics module further comprises a sensor configured to detect a marking on the flexible resistance band to identify characteristics of the flexible resistance band.

21. The system of claim 4, wherein the sensor includes a force sensor, and wherein the force sensor is anchored to the flexible resistance band in such a way that places the force sensor mechanically in series with the force input applied to the flexible resistance band by the user.

22. The system of claim 4, wherein the anchoring module is configured to clamp simultaneously to two separate locations on the flexible resistance band.

23. The system of claim 22, wherein the anchoring module introduces slack between two separate points of attachment to the flexible resistance band.

24. The system of claim 4, wherein the anchoring module is configured to be actuated through a single degree-of-freedom motion.

25. The system of claim 4, wherein the anchoring module further comprises protruding bars positioned to transmit applied forces on the flexible resistive band to the force sensor.

26. The system of claim 25, wherein the protruding bars have a profile that serves to guide the flexible resistive band to centers of the protruding bars.

27. The system of claim 4, wherein the clamping mechanism of the anchoring module further comprises a rotational or sliding hinge configured to removably secure the flexible resistive band.

28. The system of claim 1, further comprising an interface module discrete from the electronics module and configured for attachment to the user or to a fixture and to the electronics module.

29. The system of claim 4, wherein the
clamping mechanism includes at least one spring-loaded cam cleat configured for removably securing the anchoring module to the flexible resistance band.

30. A method for quantification of exercise and physical therapy using a system for quantification of exercise and physical therapy, comprising:
a plurality of modules, including:
an anchoring module equipped with a clamping mechanism including at least two protruding bars and an opposing center bar and the anchoring module further including an anchoring-module coupling fixture;
an electronics module including:
i. a processor configured to receive signals from a force sensor; and
ii. a computer storage medium storing software code and in communication with the processor, wherein the software code includes instruction for processing the signals from the force sensor to quantify a user's exercise or physical therapy; and
at least one electronics-module coupling fixture configured to secure the electronics module to the anchoring module coupling fixture, wherein at least one of the modules includes the force sensor, wherein the force sensor is configured to generate a signal representative of the user's performance during the exercise or physical therapy, the method comprising:

securing the anchoring module to a flexible resistance element using the clamping mechanism of the anchoring module;

applying a force to the flexible resistance element via performance of the exercise or physical therapy;

generating at least three reaction-force vectors with the at least two protruding bars and the opposing center bar on the flexible resistance element in response to the applied force on the flexible resistance element;

transmitting the reaction-force vector from the center bar to the force sensor;

using the force sensor to measure the reaction-force vector transmitted to the center bar to determine tensile force in the flexible resistive element and to quantify the performance of the exercise or physical therapy; and displaying a representation of the performance quantification.

31. The method of claim 30, wherein the system further comprises a displacement sensor included in at least one of the modules, and wherein the method further comprises:

using the displacement sensor to measure the displacement of the system; and displaying a representation of the displacement.

32. The method of claim 30, wherein the method further comprises:

deriving metrics selected from energy, power, smoothness of exercise motion, symmetry of the exercise motion, and other derivatives of data communicated by at least one sensor from the communicated data; and displaying a representation of the derived metrics.

33. The method of claim 32, wherein at least one of the metrics is represented by visual, audible, or haptic feedback.

34. The method of claim 30, wherein the system and data therefrom are used as an input and/or control device for games.

35. The method of claim 30, wherein the system and data therefrom are used to provide coaching feedback or to guide workouts.

36. The method of claim 30, further comprising using the measurements of applied force to track strength, cardiopulmonary, flexibility or strength exercises.

37. The method of claim 30, wherein the at least two protruding bars are rollers.

38. The method of claim 30, wherein at least one of the modules also includes an inertial measurement unit, the measurement further comprising using the inertial measurement to measure at least one of the following:

amplitude and percentage of stretch of a resistive element;
at least one of range, speed, and acceleration of motion;
orientation of the system in 3D space and trajectory of motion;
estimation of limb or body movement;
estimation of user range of movement;
repetitions during free-body motions;
amount of time a user can stay in a given position;
distance moved over ground and pace of motion during walking and/or running;
flexibility of at least one joint during a complex movement;
a user's body dimensions;
static or dynamic balance and stability;
reaction time; and
rest and recovery time.

39. The system of claim 25, wherein the protruding bars are rollers.

40. A system for quantification of exercise and physical therapy, comprising:

a plurality of modules, including:

an anchoring module equipped with a clamping mechanism including at least two protruding bars and an opposing center bar, wherein the clamping mechanism is configured to be securable to a flexible resistance element and for the protruding bars and the opposing center bar to generate at least three reaction-force vectors on the flexible resistance element when secured thereto and when a tensile force is applied to the flexible resistive element, and the anchoring module further including an anchoring-module coupling fixture;

an electronics module including:

iii. a processor configured to receive signals from a force sensor; and iv. a computer storage medium storing software code and in communication with the processor, wherein the software code includes instruction for processing the signals from the force sensor to quantify a user's exercise or physical therapy; and at least one electronics-module coupling fixture configured to secure the electronics module to the anchoring module coupling fixture, wherein at least one of the modules includes the force sensor, wherein the force sensor is configured to generate a signal representative of the user's performance during the exercise or physical therapy.

41. The system of claim 4, wherein the clamping mechanism is in the form of a spring-loaded cam cleat.

* * * * *